United States Patent
Reisinger et al.

(10) Patent No.: US 10,457,926 B2
(45) Date of Patent: Oct. 29, 2019

(54) POLYPEPTIDES HAVING XYLANASE ACTIVITY WITH A HIGH CONVERSION RATE OF XYLOSE—CONTAINING POLYSACCHARIDES

(71) Applicant: CLARIANT PRODUKTE (DEUTSCHLAND) GmbH, Frankfurt am Main (DE)

(72) Inventors: Christoph Reisinger, Munich (DE); Christian Gamauf, Munich (DE); Michael Kraus, Munich (DE); Isabel Unterstrasser, Rimsting (DE); Aleksandra Mitrovic, Graz (AT); Anton Glieder, Gleisdorf (AT)

(73) Assignee: Clariant Produkte (Deutschland) GmbH, Frankfurt am Main (DE)

( * ) Notice: Subject to any disclaimer, the term of this patent is extended or adjusted under 35 U.S.C. 154(b) by 28 days.

(21) Appl. No.: 15/507,306

(22) PCT Filed: Aug. 24, 2015

(86) PCT No.: PCT/EP2015/069351
§ 371 (c)(1),
(2) Date: Feb. 28, 2017

(87) PCT Pub. No.: WO2016/034449
PCT Pub. Date: Mar. 10, 2016

(65) Prior Publication Data
US 2017/0327809 A1   Nov. 16, 2017

(30) Foreign Application Priority Data
Sep. 2, 2014  (EP) .................................... 14003017

(51) Int. Cl.
| | | |
|---|---|---|
| *C12N 9/30* | (2006.01) |
| *C12N 15/00* | (2006.01) |
| *C12P 21/06* | (2006.01) |
| *C12P 21/04* | (2006.01) |
| *C12N 9/24* | (2006.01) |

(52) U.S. Cl.
CPC ......... *C12N 9/2482* (2013.01); *C12N 9/2402* (2013.01); *C12N 9/248* (2013.01); *C12Y 302/01008* (2013.01); *C12Y 302/01021* (2013.01); *C12Y 302/01037* (2013.01)

(58) Field of Classification Search
None
See application file for complete search history.

(56) References Cited

U.S. PATENT DOCUMENTS

| | | | | |
|---|---|---|---|---|
| 2011/0111453 A1* | 5/2011 | McBrayer | ................ | C12N 1/22 435/41 |
| 2014/0227761 A1 | 8/2014 | Spodsberg | | |

FOREIGN PATENT DOCUMENTS

| | | |
|---|---|---|
| EP | 2336152 A1 | 6/2011 |
| WO | 199727290 A1 | 1/1997 |

OTHER PUBLICATIONS

Studer. Residue mutations and their impact on protein structure and function: detecting beneficial and pathogenic changes. Residue mutations and their impact on protein structure and function: detecting beneficial and pathogenic changes. Biochem. J. (2013) 449, 581-594.*
Vladimir Elisashivili, et al.; Lignocellulose-degrading enzyme production by white-rot Basidiomycetes isolated from the forests of Georgia, World J. Microbiol Biotechnol (2009), pp. 331-339.
M.A. Larkin, et al.; ClustalW and ClustalX version 2: Bioinformatics, 2007, vol. 23(21), pp. 2947-2948.

* cited by examiner

*Primary Examiner* — Yong D Pak
(74) *Attorney, Agent, or Firm* — Verrill Dana LLP

(57) ABSTRACT

The present application provides novel polypeptides having xylanase activity and the respective nucleic acid sequences encoding those polypeptides as well as vectors comprising these nucleic acid sequences and host cells transformed by these vectors. In addition the present invention provides a method for producing these polypeptides and a composition comprising the inventive polypeptides.

10 Claims, 6 Drawing Sheets
Specification includes a Sequence Listing.

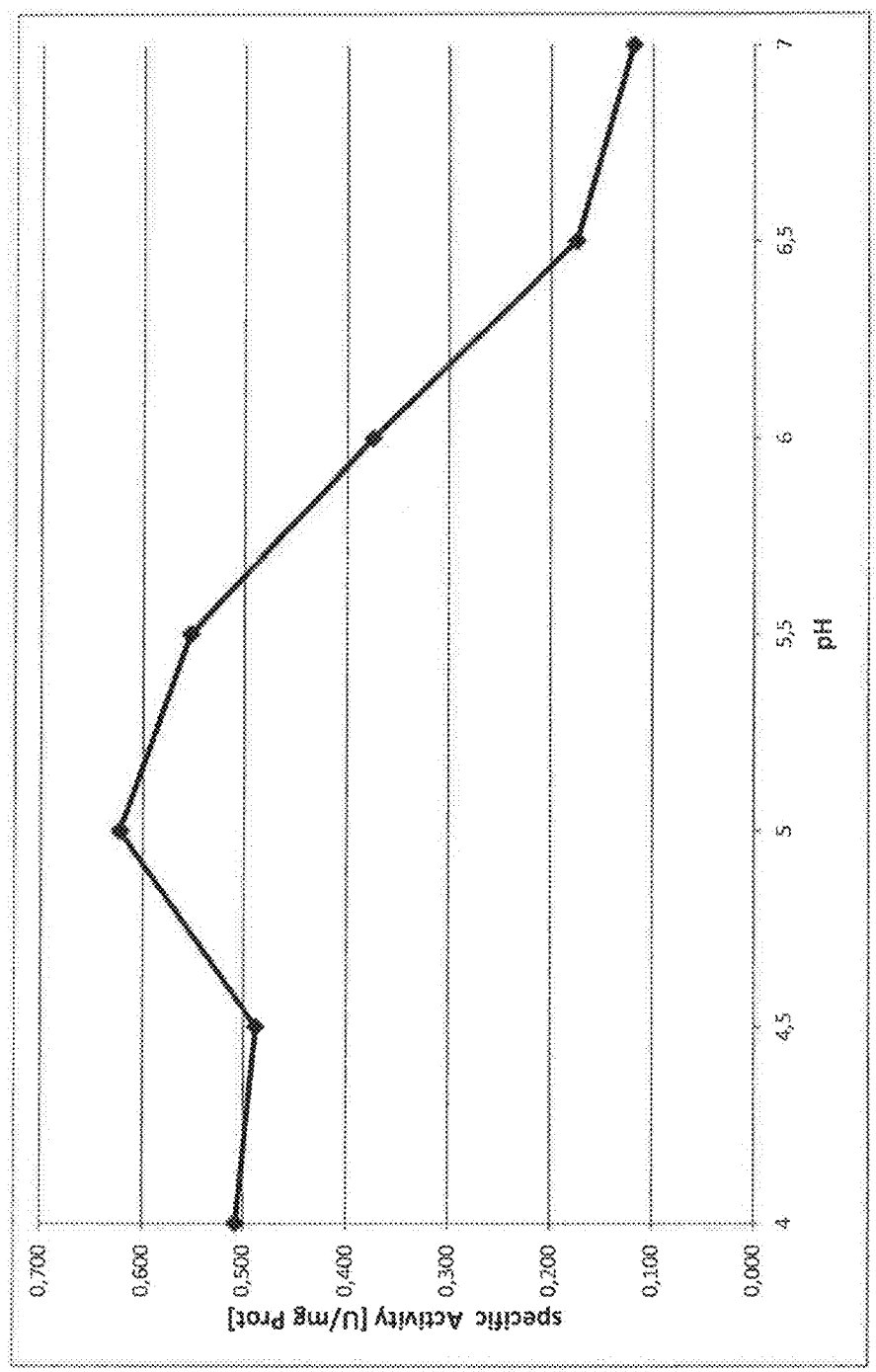

SEQUENCE LISTING

<160> NUMBER OF SEQ ID NOS: 14

<210> SEQ ID NO 1
<211> LENGTH: 1185
<212> TYPE: DNA
<213> ORGANISM: Fomes fomentarius

<400> SEQUENCE: 1

| | | | | | |
|---|---|---|---|---|---|
| atgaaggtct | ccgcagcgtt | tgctgtgctc | tttgctctcg | tcccgtacgc | ctttggtcaa | 60 |
| gcccagacat | ggggccagtg | cggtggtcaa | ggctggtcag | gacccacgac | ctgcgtgtcg | 120 |
| ggttccacct | gcacggtcat | caatgcatac | tattcgcaat | gtcttcctgt | ctctagcact | 180 |
| tctaccacca | ctggcggcac | gacaactacc | gcgacaacta | cgcctagctc | gaccgccggc | 240 |
| ttgcacacgc | ttgccaaagc | gaagggcaaa | ctgtactttg | gtagtgcgac | agataacccg | 300 |
| gaactctccg | actcggtata | cgttacgctc | ctctccaaca | caaggagtt | cggccagatc | 360 |
| actcccggca | acagcatgaa | atgggacgcg | actgagccgt | cgcgcggaac | cttccaattc | 420 |
| gcgaacggcg | acaccatcgc | caaccttgcc | aaaaacaacg | gcagctcct | gcgcggacac | 480 |
| aactgcgtgt | ggcacagcca | actcccgagc | tgggtttcga | acggcaactg | gaccgctgcg | 540 |
| gagttgactg | agatcattca | gacccactgc | agcactgttg | tcggccacta | caagggtcaa | 600 |
| atctattcgt | gggatgtcat | caacgagcca | ttcaacgagg | acggtacctg | gcgtaccagc | 660 |
| gtcttctaca | cacccctcaa | cactactttc | gtctcggtcg | cactcaaggc | cgcacgctcc | 720 |
| gcagacccgg | acgccaagct | gtacatcaac | gactacaaca | ttgagagcac | aggcgcgaag | 780 |
| tcgaccgcga | tgctgaatct | agtcaagcag | ctgcaggcgg | atggcgtgcc | catcgacggt | 840 |
| gtcggcttgc | aggcacacct | cattgttggc | tctgtcccga | cgtcgttgca | gaccgtgctg | 900 |
| gagcagttca | ccgcgctcgg | cgtcgaggtc | gcgatcacgg | agctcgacgt | caggatgacg | 960 |
| cttcccgcga | ccgatgcgct | cctcgcgcag | caggccaaag | attatcagag | tgtcgtgcag | 1020 |
| gcgtgtgcta | atgtgtccaa | gtgcgttggc | atcacgatat | gggactacac | cgacaagtac | 1080 |
| tcttgggttc | ccagcgtctt | ccaaggacag | ggtgctgctc | tcccttggga | cgagaacttc | 1140 |
| aatatcaagc | tgcgtacaa | cggcatcgtc | gcagccctga | cataa | | 1185 |

<210> SEQ ID NO 2
<211> LENGTH: 394
<212> TYPE: PRT
<213> ORGANISM: Fomes fomentarius

<400> SEQUENCE: 2

Met Lys Val Ser Ala Ala Phe Ala Val Leu Phe Ala Leu Val Pro Tyr
1               5                   10                  15

Ala Phe Gly Gln Ala Gln Thr Trp Gly Gln Cys Gly Gly Gln Gly Trp
            20                  25                  30

Ser Gly Pro Thr Thr Cys Val Ser Gly Thr Cys Thr Val Ile Asn
        35                  40                  45

Ala Tyr Tyr Ser Gln Cys Leu Pro Val Ser Ser Thr Ser Thr Thr Thr
    50                  55                  60

Gly Gly Thr Thr Thr Thr Ala Thr Thr Thr Pro Ser Ser Thr Ala Gly
65                  70                  75                  80

Leu His Thr Leu Ala Lys Ala Lys Gly Lys Leu Tyr Phe Gly Ser Ala
                85                  90                  95

Thr Asp Asn Pro Glu Leu Ser Asp Ser Val Tyr Val Thr Leu Leu Ser
            100                 105                 110

```
Asn Asn Lys Glu Phe Gly Gln Ile Thr Pro Gly Asn Ser Met Lys Trp
            115                 120                 125

Asp Ala Thr Glu Pro Ser Arg Gly Thr Phe Gln Phe Ala Asn Gly Asp
        130                 135                 140

Thr Ile Ala Asn Leu Ala Lys Asn Asn Gly Gln Leu Leu Arg Gly His
145                 150                 155                 160

Asn Cys Val Trp His Ser Gln Leu Pro Ser Trp Val Ser Asn Gly Asn
                165                 170                 175

Trp Thr Ala Ala Glu Leu Thr Glu Ile Ile Gln Thr His Cys Ser Thr
            180                 185                 190

Val Val Gly His Tyr Lys Gly Gln Ile Tyr Ser Trp Asp Val Ile Asn
        195                 200                 205

Glu Pro Phe Asn Glu Asp Gly Thr Trp Arg Thr Ser Val Phe Tyr Asn
    210                 215                 220

Thr Leu Asn Thr Thr Phe Val Ser Val Ala Leu Lys Ala Ala Arg Ser
225                 230                 235                 240

Ala Asp Pro Asp Ala Lys Leu Tyr Ile Asn Asp Tyr Asn Ile Glu Ser
                245                 250                 255

Thr Gly Ala Lys Ser Thr Ala Met Leu Asn Leu Val Lys Gln Leu Gln
            260                 265                 270

Ala Asp Gly Val Pro Ile Asp Gly Val Gly Leu Gln Ala His Leu Ile
        275                 280                 285

Val Gly Ser Val Pro Thr Ser Leu Gln Thr Val Leu Glu Gln Phe Thr
    290                 295                 300

Ala Leu Gly Val Glu Val Ala Ile Thr Glu Leu Asp Val Arg Met Thr
305                 310                 315                 320

Leu Pro Ala Thr Asp Ala Leu Leu Ala Gln Gln Ala Lys Asp Tyr Gln
                325                 330                 335

Ser Val Val Gln Ala Cys Ala Asn Val Ser Lys Cys Val Gly Ile Thr
            340                 345                 350

Ile Trp Asp Tyr Thr Asp Lys Tyr Ser Trp Val Pro Ser Val Phe Gln
        355                 360                 365

Gly Gln Gly Ala Ala Leu Pro Trp Asp Glu Asn Phe Asn Ile Lys Pro
    370                 375                 380

Ala Tyr Asn Gly Ile Val Ala Ala Leu Thr
385                 390

<210> SEQ ID NO 3
<211> LENGTH: 1128
<212> TYPE: DNA
<213> ORGANISM: Fomes fomentarius

<400> SEQUENCE: 3
caagcccaga catggggcca gtgcggtggt caaggctggt caggacccac gacctgcgtg      60
tcgggttcca cctgcacggt catcaatgca ctattcgc aatgtcttcc tgtctctagc      120
acttctacca ccactggcgg cacgacaact accgcgacaa ctacgcctag ctcgaccgcc      180
ggcttgcaca cgcttgccaa agcgaagggc aaactgtact tggtagtgc acagataac       240 ccggaactct ccgactcggt atacgttacg ctcctctcca acaacaagga gttcggccag      300
atcactcccg gcaacagcat gaaatgggac gcgactgagc cgtcgcgcgg aaccttccaa      360
ttcgcgaacg gcgacaccat cgccaacctt gccaaaaaca acgggcagct cctgcgcgga      420
cacaactgcg tgtggcacag ccaactcccg agctgggttt cgaacggcaa ctggaccgct      480
gcggagttga ctgagatcat tcagacccac tgcagcactg ttgtcggcca ctacaagggt      540
```

```
caaatctatt cgtgggatgt catcaacgag ccattcaacg aggacggtac ctggcgtacc    600
agcgtcttct acaacaccct caacactact ttcgtctcgg tcgcactcaa ggccgcacgc    660
tccgcagacc cggacgccaa gctgtacatc aacgactaca acattgagag cacaggcgcg    720
aagtcgaccg cgatgctgaa tctagtcaag cagctgcagg cggatggcgt gcccatcgac    780
ggtgtcggct tgcaggcaca cctcattgtt ggctctgtcc cgacgtcgtt gcagaccgtg    840
ctggagcagt tcaccgcgct cggcgtcgag gtcgcgatca cggagctcga cgtcaggatg    900
acgcttcccg cgaccgatgc gctcctcgcg cagcaggcca agattatca gagtgtcgtg    960 caggcgtgtg ctaatgtgtc caagtgcgtt ggcatcacga tatgggacta caccgacaag   1020
tactcttggg ttcccagcgt cttccaagga cagggtgctg ctctcccttg ggacgagaac   1080
ttcaatatca agcctgcgta caacggcatc gtcgcagccc tgacataa                1128
```

<210> SEQ ID NO 4
<211> LENGTH: 375
<212> TYPE: PRT
<213> ORGANISM: Fomes fomentarius

<400> SEQUENCE: 4

```
Gln Ala Gln Thr Trp Gly Gln Cys Gly Gly Gln Gly Trp Ser Gly Pro
1               5                   10                  15

Thr Thr Cys Val Ser Gly Ser Thr Cys Thr Val Ile Asn Ala Tyr Tyr
            20                  25                  30

Ser Gln Cys Leu Pro Val Ser Ser Thr Ser Thr Thr Gly Gly Thr
        35                  40                  45

Thr Thr Thr Ala Thr Thr Thr Pro Ser Ser Thr Ala Gly Leu His Thr
    50                  55                  60

Leu Ala Lys Ala Lys Gly Lys Leu Tyr Phe Gly Ser Ala Thr Asp Asn
65                  70                  75                  80

Pro Glu Leu Ser Asp Ser Val Tyr Val Thr Leu Leu Ser Asn Asn Lys
                85                  90                  95

Glu Phe Gly Gln Ile Thr Pro Gly Asn Ser Met Lys Trp Asp Ala Thr
            100                 105                 110

Glu Pro Ser Arg Gly Thr Phe Gln Phe Ala Asn Gly Asp Thr Ile Ala
        115                 120                 125

Asn Leu Ala Lys Asn Asn Gly Gln Leu Leu Arg Gly His Asn Cys Val
    130                 135                 140

Trp His Ser Gln Leu Pro Ser Trp Val Ser Asn Gly Asn Trp Thr Ala
145                 150                 155                 160

Ala Glu Leu Thr Glu Ile Ile Gln Thr His Cys Ser Thr Val Val Gly
                165                 170                 175

His Tyr Lys Gly Gln Ile Tyr Ser Trp Asp Val Ile Asn Glu Pro Phe
            180                 185                 190

Asn Glu Asp Gly Thr Trp Arg Thr Ser Val Phe Tyr Asn Thr Leu Asn
        195                 200                 205

Thr Thr Phe Val Ser Val Ala Leu Lys Ala Ala Arg Ser Ala Asp Pro
    210                 215                 220

Asp Ala Lys Leu Tyr Ile Asn Asp Tyr Asn Ile Glu Ser Thr Gly Ala
225                 230                 235                 240

Lys Ser Thr Ala Met Leu Asn Leu Val Lys Gln Leu Gln Ala Asp Gly
                245                 250                 255

Val Pro Ile Asp Gly Val Gly Leu Gln Ala His Leu Ile Val Gly Ser
            260                 265                 270
```

Val Pro Thr Ser Leu Gln Thr Val Leu Glu Gln Phe Thr Ala Leu Gly
            275                 280                 285

Val Glu Val Ala Ile Thr Glu Leu Asp Val Arg Met Thr Leu Pro Ala
            290                 295                 300

Thr Asp Ala Leu Leu Ala Gln Gln Ala Lys Asp Tyr Gln Ser Val Val
305                 310                 315                 320

Gln Ala Cys Ala Asn Val Ser Lys Cys Val Gly Ile Thr Ile Trp Asp
                325                 330                 335

Tyr Thr Asp Lys Tyr Ser Trp Val Pro Ser Val Phe Gln Gly Gln Gly
                340                 345                 350

Ala Ala Leu Pro Trp Asp Glu Asn Phe Asn Ile Lys Pro Ala Tyr Asn
            355                 360                 365

Gly Ile Val Ala Ala Leu Thr
            370                 375

<210> SEQ ID NO 5
<211> LENGTH: 1206
<212> TYPE: DNA
<213> ORGANISM: Artificial sequence
<220> FEATURE:
<223> OTHER INFORMATION: Artificial sequence coding tFfXyn1 mature
      protein fusion with the Trichoderma reesei CBHI signal peptide and
      C-terminal 6x-His-TAG

<400> SEQUENCE: 5

| | |
|---|---:|
| atgtatcgga agttggccgt catctcggcc ttcttggcca cagcacgggc tcaagcccag | 60 |
| acatggggcc agtgcggtgg tcaaggctgg tcaggaccca cgacctgcgt gtcgggttcc | 120 |
| acctgcacgg tcatcaatgc atactattcg caatgtcttc ctgtctctag cacttctacc | 180 |
| accactggcg gcacgacaac taccgcgaca actacgccta gctcgaccgc cggcttgcac | 240 |
| acgcttgcca agcgaagggc aaactgtac tttggtagtg cgacagataa cccggaactc | 300 |
| tccgactcgg tatacgttac gctcctctcc aacaacaagg agttcggcca gatcactccc | 360 |
| ggcaacagca tgaaatggga cgcgactgag ccgtcgcgcg gaaccttcca attcgcgaac | 420 |
| ggcgacacca tcgccaacct tgccaaaaac aacgggcagc tcctgcgcgg acacaactgc | 480 |
| gtgtggcaca gccaactccc gagctgggtt tcgaacggca actggaccgc tgcggagttg | 540 |
| actgagatca ttcagaccca ctgcagcact gttgtcggcc actacaaggg tcaaatctat | 600 |
| tcgtgggatg tcatcaacga gccattcaac gaggacggta cctggcgtac cagcgtcttc | 660 |
| tacaacaccc tcaacactac tttcgtctcg gtcgcactca aggccgcacg ctccgcagac | 720 |
| ccggacgcca agctgtacat caacgactac aacattgaga gcacaggcgc gaagtcgacc | 780 |
| gcgatgctga atctagtcaa gcagctgcag gcggatggcg tgcccatcga cggtgtcggc | 840 |
| ttgcaggcac acctcattgt tggctctgtc ccgacgtcgt tgcagaccgt gctggagcag | 900 |
| ttcaccgcgc tcggcgtcga ggtcgcgatc acggagctcg acgtcaggat gacgcttccc | 960 |
| gcgaccgatg cgctcctcgc gcagcaggcc aaagattatc agagtgtcgt gcaggcgtgt | 1020 |
| gctaatgtgt ccaagtgcgt tggcatcacg atatgggact acaccgacaa gtactcttgg | 1080 |
| gttcccagcg tcttccaagg acagggtgct gctctcccct gggacgagaa cttcaatatc | 1140 |
| aagcctgcgt acaacggcat cgtcgcagcc ctgacaggat ctggccatca ccaccatcat | 1200 |
| cactaa | 1206 |

<210> SEQ ID NO 6
<211> LENGTH: 1431

<212> TYPE: DNA
<213> ORGANISM: Artificial sequence
<220> FEATURE:
<223> OTHER INFORMATION: Artificial sequence coding yFfXyn1 mature
      protein fusion with the Saccharomyces cerevisiae MFalpha signal
      peptide and C-terminal 6x-HIS-TAG

<400> SEQUENCE: 6

```
atgagatttc cttcaatttt tactgcagtt ttattcgcag catcctccgc attagctgct    60
ccagtcaaca ctacaacaga agatgaaacg gcacaaattc cggctgaagc tgtcatcggt   120
tacttagatt tagaagggga tttcgatgtt gctgttttgc cattttccaa cagcacaaat   180
aacgggttat tgtttataaa tactactatt gccagcattg ctgctaaaga agaagggta    240
tctttggata aacgtgaggc ggaagcaccc tctcaagccc agacatgggg ccagtgcggt   300
ggtcaaggct ggtcaggacc cacgacctgc gtgtcgggtt ccacctgcac ggtcatcaat   360
gcatactatt cgcaatgtct tcctgtctct agcacttcta ccaccactgg cggcacgaca   420
actaccgcga caactacgcc tagctcgacc gccggcttgc acacgcttgc aaaagcgaag   480
ggcaaactgt actttggtag tgcgacagat aacccggaac tctccgactc ggtatacgtt   540
acgctcctct ccaacaacaa ggagttcggc cagatcactc ccggcaacag catgaaatgg   600
gacgcgactg agccgtcgcg cggaaccttc caattcgcga acgcgacac catcgccaac   660
cttgccaaaa caacgggca gctcctgcgc ggacacaact cgtgtggca cagccaactc   720
ccgagctggg tttcgaacgg caactggacc gctgcggagt tgactgagat cattcagacc   780
cactgcagca ctgttgtcgg ccactacaag ggtcaaatct attcgtggga tgtcatcaac   840
gagccattca acgaggacgg tacctggcgt accagcgtct tctacaacac cctcaacact   900
actttcgtct cggtcgcact caaggccgca cgctccgcag acccggacgc caagctgtac   960
atcaacgact acaacattga gagcacaggc gcgaagtcga ccgcgatgct gaatctagtc  1020
aagcagctgc aggcggatgg cgtgcccatc gacggtgtcg gcttgcaggc acacctcatt  1080
gttggctctg tcccgacgtc gttgcagacc gtgctggagc agttcaccgc gctcggcgtc  1140
gaggtcgcga tcacggagct cgacgtcagg atgacgcttc ccgcgaccga tgcgctcctc  1200
gcgcagcagg ccaaagatta tcagagtgtc gtgcaggcgt gtgctaatgt gtccaagtgc  1260
gttggcatca cgatatggga ctacaccgac aagtactctt gggttcccag cgtcttccaa  1320
ggacagggtg ctgctctccc ttgggacgag aacttcaata tcaagcctgc gtacaacggc  1380
atcgtcgcag ccctgacagg atctggccat caccaccatc atcactaata a           1431
```

<210> SEQ ID NO 7
<211> LENGTH: 384
<212> TYPE: PRT
<213> ORGANISM: Artificial sequence
<220> FEATURE:
<223> OTHER INFORMATION: tFfXyn1 mature protein fusion with the
      Trichoderma reesei CBHI signal peptide and C-terminal 6x-His-TAG

<400> SEQUENCE: 7

```
Gln Ala Gln Thr Trp Gly Gln Cys Gly Gly Gln Gly Trp Ser Gly Pro
1               5                   10                  15

Thr Thr Cys Val Ser Gly Ser Thr Cys Thr Val Ile Asn Ala Tyr Tyr
            20                  25                  30

Ser Gln Cys Leu Pro Val Ser Ser Thr Ser Thr Thr Gly Gly Thr
        35                  40                  45

Thr Thr Thr Ala Thr Thr Thr Pro Ser Ser Thr Ala Gly Leu His Thr
    50                  55                  60
```

Leu Ala Lys Ala Lys Gly Lys Leu Tyr Phe Gly Ser Ala Thr Asp Asn
65                  70                  75                  80

Pro Glu Leu Ser Asp Ser Val Tyr Val Thr Leu Leu Ser Asn Asn Lys
            85                  90                  95

Glu Phe Gly Gln Ile Thr Pro Gly Asn Ser Met Lys Trp Asp Ala Thr
            100                 105                 110

Glu Pro Ser Arg Gly Thr Phe Gln Phe Ala Asn Gly Asp Thr Ile Ala
            115                 120                 125

Asn Leu Ala Lys Asn Asn Gly Gln Leu Leu Arg Gly His Asn Cys Val
            130                 135                 140

Trp His Ser Gln Leu Pro Ser Trp Val Ser Asn Gly Asn Trp Thr Ala
145                 150                 155                 160

Ala Glu Leu Thr Glu Ile Ile Gln Thr His Cys Ser Thr Val Val Gly
                165                 170                 175

His Tyr Lys Gly Gln Ile Tyr Ser Trp Asp Val Ile Asn Glu Pro Phe
                180                 185                 190

Asn Glu Asp Gly Thr Trp Arg Thr Ser Val Phe Tyr Asn Thr Leu Asn
            195                 200                 205

Thr Thr Phe Val Ser Val Ala Leu Lys Ala Ala Arg Ser Ala Asp Pro
210                 215                 220

Asp Ala Lys Leu Tyr Ile Asn Asp Tyr Asn Ile Glu Ser Thr Gly Ala
225                 230                 235                 240

Lys Ser Thr Ala Met Leu Asn Leu Val Lys Gln Leu Gln Ala Asp Gly
                245                 250                 255

Val Pro Ile Asp Gly Val Gly Leu Gln Ala His Leu Ile Val Gly Ser
            260                 265                 270

Val Pro Thr Ser Leu Gln Thr Val Leu Glu Gln Phe Thr Ala Leu Gly
            275                 280                 285

Val Glu Val Ala Ile Thr Glu Leu Asp Val Arg Met Thr Leu Pro Ala
290                 295                 300

Thr Asp Ala Leu Leu Ala Gln Gln Ala Lys Asp Tyr Gln Ser Val Val
305                 310                 315                 320

Gln Ala Cys Ala Asn Val Ser Lys Cys Val Gly Ile Thr Ile Trp Asp
                325                 330                 335

Tyr Thr Asp Lys Tyr Ser Trp Val Pro Ser Val Phe Gln Gly Gln Gly
            340                 345                 350

Ala Ala Leu Pro Trp Asp Glu Asn Phe Asn Ile Lys Pro Ala Tyr Asn
            355                 360                 365

Gly Ile Val Ala Ala Leu Thr Gly Ser Gly His His His His His His
370                 375                 380

<210> SEQ ID NO 8
<211> LENGTH: 216
<212> TYPE: PRT
<213> ORGANISM: Thermomyces lanuginosus

<400> SEQUENCE: 8

Ser Phe Pro Ala Gly Asn Ala Thr Glu Leu Glu Lys Arg Gln Thr Thr
1               5                   10                  15

Pro Asn Ser Glu Gly Trp His Asp Gly Tyr Tyr Tyr Ser Trp Trp Ser
            20                  25                  30

Asp Gly Gly Ala Gln Ala Thr Tyr Thr Asn Leu Glu Gly Gly Thr Tyr
            35                  40                  45

Glu Ile Ser Trp Gly Asp Gly Gly Asn Leu Val Gly Gly Lys Gly Trp

```
            50                  55                  60
Asn Pro Gly Leu Asn Ala Arg Ala Ile His Phe Glu Gly Val Tyr Gln
 65                  70                  75                  80

Pro Asn Gly Asn Ser Tyr Leu Ala Val Tyr Gly Trp Thr Arg Asn Pro
                 85                  90                  95

Leu Val Glu Tyr Tyr Ile Val Glu Asn Phe Gly Thr Tyr Asp Pro Ser
            100                 105                 110

Ser Gly Ala Thr Asp Leu Gly Thr Val Glu Cys Asp Gly Ser Ile Tyr
            115                 120                 125

Arg Leu Gly Lys Thr Thr Arg Val Asn Ala Pro Ser Ile Asp Gly Thr
            130                 135                 140

Gln Thr Phe Asp Gln Tyr Trp Ser Val Arg Gln Asp Lys Arg Thr Ser
145                 150                 155                 160

Gly Thr Val Gln Thr Gly Cys His Phe Asp Ala Trp Ala Arg Ala Gly
                165                 170                 175

Leu Asn Val Asn Gly Asp His Tyr Tyr Gln Ile Val Ala Thr Glu Gly
                180                 185                 190

Tyr Phe Ser Ser Gly Tyr Ala Arg Ile Thr Val Ala Asp Val Gly Gly
                195                 200                 205

Ser Gly His His His His His His
            210                 215

<210> SEQ ID NO 9
<211> LENGTH: 215
<212> TYPE: PRT
<213> ORGANISM: Trichoderma reesei

<400> SEQUENCE: 9

Ser Cys Arg Pro Ala Ala Glu Val Glu Ser Val Ala Val Glu Lys Arg
  1               5                  10                  15

Gln Thr Ile Gln Pro Gly Thr Gly Tyr Asn Asn Gly Tyr Phe Tyr Ser
             20                  25                  30

Tyr Trp Asn Asp Gly His Gly Gly Val Thr Tyr Thr Asn Gly Pro Gly
         35                  40                  45

Gly Gln Phe Ser Val Asn Trp Ser Asn Ser Gly Asn Phe Val Gly Gly
     50                  55                  60

Lys Gly Trp Gln Pro Gly Thr Lys Asn Lys Val Ile Asn Phe Ser Gly
 65                  70                  75                  80

Ser Tyr Asn Pro Asn Gly Asn Ser Tyr Leu Ser Val Tyr Gly Trp Ser
                 85                  90                  95

Arg Asn Pro Leu Ile Glu Tyr Tyr Ile Val Glu Asn Phe Gly Thr Tyr
            100                 105                 110

Asn Pro Ser Thr Gly Ala Thr Lys Leu Gly Glu Val Thr Ser Asp Gly
            115                 120                 125

Ser Val Tyr Asp Ile Tyr Arg Thr Gln Arg Val Asn Gln Pro Ser Ile
            130                 135                 140

Ile Gly Thr Ala Thr Phe Tyr Gln Tyr Trp Ser Val Arg Arg Asn His
145                 150                 155                 160

Arg Ser Ser Gly Ser Val Asn Thr Ala Asn His Phe Asn Ala Trp Ala
                165                 170                 175

Gln Gln Gly Leu Thr Leu Gly Thr Met Asp Tyr Gln Ile Val Ala Val
            180                 185                 190

Glu Gly Tyr Phe Ser Ser Gly Ser Ala Ser Ile Thr Val Ser Gly Ser
            195                 200                 205
```

```
Gly His His His His His
    210             215

<210> SEQ ID NO 10
<211> LENGTH: 219
<212> TYPE: PRT
<213> ORGANISM: Trichoderma reesei

<400> SEQUENCE: 10

Met Pro Thr Gly Leu Glu Pro Glu Ser Ser Val Asn Val Thr Glu Arg
1               5                   10                  15

Gly Met Tyr Asp Phe Val Leu Gly Ala His Asn Asp His Arg Arg Arg
            20                  25                  30

Ala Ser Ile Asn Tyr Asp Gln Asn Tyr Gln Thr Gly Gly Gln Val Ser
        35                  40                  45

Tyr Ser Pro Ser Asn Thr Gly Phe Ser Val Asn Trp Asn Thr Gln Asp
    50                  55                  60

Asp Phe Val Val Gly Val Gly Trp Thr Thr Gly Ser Ser Ala Pro Ile
65                  70                  75                  80

Asn Phe Gly Gly Ser Phe Ser Val Asn Ser Gly Thr Gly Leu Leu Ser
                85                  90                  95

Val Tyr Gly Trp Ser Thr Asn Pro Leu Val Glu Tyr Tyr Ile Met Glu
            100                 105                 110

Asp Asn His Asn Tyr Pro Ala Gln Gly Thr Val Lys Gly Thr Val Thr
        115                 120                 125

Ser Asp Gly Ala Thr Tyr Thr Ile Trp Glu Asn Thr Arg Val Asn Glu
    130                 135                 140

Pro Ser Ile Gln Gly Thr Ala Thr Phe Asn Gln Tyr Ile Ser Val Arg
145                 150                 155                 160

Asn Ser Pro Arg Thr Ser Gly Thr Val Thr Val Gln Asn His Phe Asn
                165                 170                 175

Ala Trp Ala Ser Leu Gly Leu His Leu Gly Gln Met Asn Tyr Gln Val
            180                 185                 190

Val Ala Val Glu Gly Trp Gly Gly Ser Gly Ser Ala Ser Gln Ser Val
        195                 200                 205

Ser Asn Gly Ser Gly His His His His His
    210                 215

<210> SEQ ID NO 11
<211> LENGTH: 465
<212> TYPE: PRT
<213> ORGANISM: Trichoderma reesei

<400> SEQUENCE: 11

Trp Ser Tyr Ala Thr Lys Ser Gln Tyr Arg Ala Asn Ile Lys Ile Asn
1               5                   10                  15

Ala Arg Gln Thr Tyr Gln Thr Met Ile Gly Gly Cys Ser Gly Ala
            20                  25                  30

Phe Gly Ile Ala Cys Gln Gln Phe Gly Ser Ser Gly Leu Ser Pro Glu
        35                  40                  45

Asn Gln Gln Lys Val Thr Gln Ile Leu Phe Asp Glu Asn Ile Gly Gly
    50                  55                  60

Leu Ser Ile Val Arg Asn Asp Ile Gly Ser Ser Pro Gly Thr Thr Ile
65                  70                  75                  80

Leu Pro Thr Cys Pro Ala Thr Pro Gln Asp Lys Phe Asp Tyr Val Trp
                85                  90                  95
```

```
Asp Gly Ser Asp Asn Cys Gln Phe Asn Leu Thr Lys Thr Ala Leu Lys
            100                 105                 110

Tyr Asn Pro Asn Leu Tyr Val Tyr Ala Asp Ala Trp Ser Ala Pro Gly
        115                 120                 125

Cys Met Lys Thr Val Gly Thr Glu Asn Leu Gly Gly Gln Ile Cys Gly
    130                 135                 140

Val Arg Gly Thr Asp Cys Lys His Asp Trp Arg Gln Ala Tyr Ala Asp
145                 150                 155                 160

Tyr Leu Val Gln Tyr Val Arg Phe Tyr Lys Glu Glu Gly Ile Asp Ile
                165                 170                 175

Ser Leu Leu Gly Ala Trp Asn Glu Pro Asp Phe Asn Pro Phe Thr Tyr
            180                 185                 190

Glu Ser Met Leu Ser Asp Gly Tyr Gln Ala Lys Asp Phe Leu Glu Val
        195                 200                 205

Leu Tyr Pro Thr Leu Lys Lys Ala Phe Pro Lys Val Asp Val Ser Cys
    210                 215                 220

Cys Asp Ala Thr Gly Ala Arg Gln Glu Arg Asn Ile Leu Tyr Glu Leu
225                 230                 235                 240

Gln Gln Ala Gly Gly Glu Arg Tyr Phe Asp Ile Ala Thr Trp His Asn
                245                 250                 255

Tyr Gln Ser Asn Pro Glu Arg Pro Phe Asn Ala Gly Gly Lys Pro Asn
            260                 265                 270

Ile Gln Thr Glu Trp Ala Asp Gly Thr Gly Pro Trp Asn Ser Thr Trp
        275                 280                 285

Asp Tyr Ser Gly Gln Leu Ala Glu Gly Leu Gln Trp Ala Leu Tyr Met
    290                 295                 300

His Asn Ala Phe Val Asn Ser Asp Thr Ser Gly Tyr Thr His Trp Trp
305                 310                 315                 320

Cys Ala Gln Asn Thr Asn Gly Asp Asn Ala Leu Ile Arg Leu Asp Arg
                325                 330                 335

Asp Ser Tyr Glu Val Ser Ala Arg Leu Trp Ala Phe Ala Gln Tyr Phe
            340                 345                 350

Arg Phe Ala Arg Pro Gly Ser Val Arg Ile Gly Ala Thr Ser Asp Val
        355                 360                 365

Glu Asn Val Tyr Val Thr Ala Tyr Val Asn Lys Asn Gly Thr Val Ala
    370                 375                 380

Ile Pro Val Ile Asn Ala Ala His Phe Pro Tyr Asp Leu Thr Ile Asp
385                 390                 395                 400

Leu Glu Gly Ile Lys Lys Arg Lys Leu Ser Glu Tyr Leu Thr Asp Asn
                405                 410                 415

Ser His Asn Val Thr Leu Gln Ser Arg Tyr Lys Val Ser Gly Ser Ser
            420                 425                 430

Leu Lys Val Thr Val Glu Pro Arg Ala Met Lys Thr Phe Trp Leu Glu
        435                 440                 445

Pro Gln Ser Thr Phe Ala Val Ile Gly Ser Gly His His His His His
    450                 455                 460

His
465

<210> SEQ ID NO 12
<211> LENGTH: 777
<212> TYPE: PRT
<213> ORGANISM: Trichoderma reesei

<400> SEQUENCE: 12
```

```
Gln Asn Asn Gln Thr Tyr Ala Asn Tyr Ser Ala Gln Gly Gln Pro Asp
1               5                   10                  15

Leu Tyr Pro Glu Thr Leu Ala Thr Leu Thr Leu Ser Phe Pro Asp Cys
            20                  25                  30

Glu His Gly Pro Leu Lys Asn Asn Leu Val Cys Asp Ser Ser Ala Gly
        35                  40                  45

Tyr Val Glu Arg Ala Gln Ala Leu Ile Ser Leu Phe Thr Leu Glu Glu
    50                  55                  60

Leu Ile Leu Asn Thr Gln Asn Ser Gly Pro Gly Val Pro Arg Leu Gly
65                  70                  75                  80

Leu Pro Asn Tyr Gln Val Trp Asn Glu Ala Leu His Gly Leu Asp Arg
            85                  90                  95

Ala Asn Phe Ala Thr Lys Gly Gly Gln Phe Glu Trp Ala Thr Ser Phe
            100                 105                 110

Pro Met Pro Ile Leu Thr Thr Ala Ala Leu Asn Arg Thr Leu Ile His
        115                 120                 125

Gln Ile Ala Asp Ile Ile Ser Thr Gln Ala Arg Ala Phe Ser Asn Ser
130                 135                 140

Gly Arg Tyr Gly Leu Asp Val Tyr Ala Pro Asn Val Asn Gly Phe Arg
145                 150                 155                 160

Ser Pro Leu Trp Gly Arg Gly Gln Glu Thr Pro Gly Glu Asp Ala Phe
            165                 170                 175

Phe Leu Ser Ser Ala Tyr Thr Tyr Glu Tyr Ile Thr Gly Ile Gln Gly
            180                 185                 190

Gly Val Asp Pro Glu His Leu Lys Val Ala Ala Thr Val Lys His Phe
        195                 200                 205

Ala Gly Tyr Asp Leu Glu Asn Trp Asn Asn Gln Ser Arg Leu Gly Phe
210                 215                 220

Asp Ala Ile Ile Thr Gln Gln Asp Leu Ser Glu Tyr Tyr Thr Pro Gln
225                 230                 235                 240

Phe Leu Ala Ala Ala Arg Tyr Ala Lys Ser Arg Ser Leu Met Cys Ala
            245                 250                 255

Tyr Asn Ser Val Asn Gly Val Pro Ser Cys Ala Asn Ser Phe Phe Leu
            260                 265                 270

Gln Thr Leu Leu Arg Glu Ser Trp Gly Phe Pro Glu Trp Gly Tyr Val
        275                 280                 285

Ser Ser Asp Cys Asp Ala Val Tyr Asn Val Phe Asn Pro His Asp Tyr
        290                 295                 300

Ala Ser Asn Gln Ser Ser Ala Ala Ser Ser Leu Arg Ala Gly Thr
305                 310                 315                 320

Asp Ile Asp Cys Gly Gln Thr Tyr Pro Trp His Leu Asn Glu Ser Phe
            325                 330                 335

Val Ala Gly Glu Val Ser Arg Gly Glu Ile Glu Arg Ser Val Thr Arg
            340                 345                 350

Leu Tyr Ala Asn Leu Val Arg Leu Gly Tyr Phe Asp Lys Lys Asn Gln
            355                 360                 365

Tyr Arg Ser Leu Gly Trp Lys Asp Val Val Lys Thr Asp Ala Trp Asn
            370                 375                 380

Ile Ser Tyr Glu Ala Ala Val Glu Gly Ile Val Leu Leu Lys Asn Asp
385                 390                 395                 400

Gly Thr Leu Pro Leu Ser Lys Lys Val Arg Ser Ile Ala Leu Ile Gly
                405                 410                 415
```

Pro Trp Ala Asn Ala Thr Thr Gln Met Gln Gly Asn Tyr Tyr Gly Pro
             420                 425                 430

Ala Pro Tyr Leu Ile Ser Pro Leu Glu Ala Ala Lys Lys Ala Gly Tyr
     435                 440                 445

His Val Asn Phe Glu Leu Gly Thr Glu Ile Ala Gly Asn Ser Thr Thr
 450                 455                 460

Gly Phe Ala Lys Ala Ile Ala Ala Lys Lys Ser Asp Ala Ile Ile
465                 470                 475                 480

Tyr Leu Gly Gly Ile Asp Asn Thr Ile Glu Gln Glu Gly Ala Asp Arg
                 485                 490                 495

Thr Asp Ile Ala Trp Pro Gly Asn Gln Leu Asp Leu Ile Lys Gln Leu
             500                 505                 510

Ser Glu Val Gly Lys Pro Leu Val Leu Gln Met Gly Gly Gly Gln
         515                 520                 525

Val Asp Ser Ser Ser Leu Lys Ser Asn Lys Lys Val Asn Ser Leu Val
 530                 535                 540

Trp Gly Gly Tyr Pro Gly Gln Ser Gly Gly Val Ala Leu Phe Asp Ile
545                 550                 555                 560

Leu Ser Gly Lys Arg Ala Pro Ala Gly Arg Leu Val Thr Thr Gln Tyr
                 565                 570                 575

Pro Ala Glu Tyr Val His Gln Phe Pro Gln Asn Asp Met Asn Leu Arg
             580                 585                 590

Pro Asp Gly Lys Ser Asn Pro Gly Gln Thr Tyr Ile Trp Tyr Thr Gly
         595                 600                 605

Lys Pro Val Tyr Glu Phe Gly Ser Gly Leu Phe Tyr Thr Thr Phe Lys
 610                 615                 620

Glu Thr Leu Ala Ser His Pro Lys Ser Leu Lys Phe Asn Thr Ser Ser
625                 630                 635                 640

Ile Leu Ser Ala Pro His Pro Gly Tyr Thr Tyr Ser Glu Gln Ile Pro
                 645                 650                 655

Val Phe Thr Phe Glu Ala Asn Ile Lys Asn Ser Gly Lys Thr Glu Ser
             660                 665                 670

Pro Tyr Thr Ala Met Leu Phe Val Arg Thr Ser Asn Ala Gly Pro Ala
         675                 680                 685

Pro Tyr Pro Asn Lys Trp Leu Val Gly Phe Asp Arg Leu Ala Asp Ile
 690                 695                 700

Lys Pro Gly His Ser Ser Lys Leu Ser Ile Pro Ile Pro Val Ser Ala
705                 710                 715                 720

Leu Ala Arg Val Asp Ser His Gly Asn Arg Ile Val Tyr Pro Gly Lys
                 725                 730                 735

Tyr Glu Leu Ala Leu Asn Thr Asp Glu Ser Val Lys Leu Glu Phe Glu
             740                 745                 750

Leu Val Gly Glu Glu Val Thr Ile Glu Asn Trp Pro Leu Glu Glu Gln
         755                 760                 765

Gln Ile Lys Asp Ala Thr Pro Asp Ala
 770                 775

<210> SEQ ID NO 13
<211> LENGTH: 849
<212> TYPE: PRT
<213> ORGANISM: Talaromyces emersonii

<400> SEQUENCE: 13

Ser Glu Asn Leu Ala Tyr Ser Pro Pro Phe Tyr Pro Ser Pro Trp Ala
1               5                   10                  15

```
Asn Gly Gln Gly Asp Trp Ala Glu Ala Tyr Glu Lys Ala Val Lys Phe
            20                  25                  30
Val Ser Gln Leu Thr Leu Ala Glu Lys Val Asn Leu Thr Thr Gly Thr
                35                  40                  45
Gly Trp Glu Gln Asp Arg Cys Val Gly Gln Val Gly Ser Ile Pro Arg
 50                  55                  60
Leu Gly Phe Pro Gly Leu Cys Met Gln Asp Ser Pro Leu Gly Val Arg
 65                  70                  75                  80
Asp Thr Asp Tyr Asn Ser Ala Phe Pro Ala Gly Val Asn Val Ala Ala
                85                  90                  95
Thr Trp Asn Arg Asp Leu Ala Tyr Arg Arg Gly Gln Ala Met Gly Glu
                100                 105                 110
Glu His Arg Gly Lys Gly Val Asp Val Gln Leu Gly Pro Val Ala Gly
                115                 120                 125
Pro Leu Gly Arg Ser Pro Asp Ala Gly Arg Asn Trp Glu Gly Phe Ala
130                 135                 140
Pro Asp Pro Val Leu Thr Gly Asn Met Met Ala Ser Thr Ile Gln Gly
145                 150                 155                 160
Ile Gln Asp Ala Gly Val Ile Ala Cys Ala Lys His Phe Ile Leu Tyr
                165                 170                 175
Glu Gln Glu His Phe Arg Gln Gly Ala Gln Asp Gly Tyr Asp Ile Ser
                180                 185                 190
Asp Ser Ile Ser Ala Asn Ala Asp Asp Lys Thr Met His Glu Leu Tyr
                195                 200                 205
Leu Trp Pro Phe Ala Asp Ala Val Arg Ala Gly Val Gly Ser Ile Met
                210                 215                 220
Cys Ser Tyr Asn Gln Val Asn Asn Ser Tyr Ala Cys Ser Asn Ser Tyr
225                 230                 235                 240
Thr Met Asn Lys Leu Leu Lys Ser Glu Leu Gly Phe Gln Gly Phe Val
                245                 250                 255
Met Thr Asp Trp Gly Gly His His Ser Gly Val Gly Ser Ala Leu Ala
                260                 265                 270
Gly Leu Asp Met Ser Met Pro Gly Asp Ile Ala Phe Asp Ser Gly Thr
                275                 280                 285
Ser Phe Trp Gly Thr Asn Leu Thr Val Ala Val Leu Asn Gly Ser Val
                290                 295                 300
Pro Glu Trp Arg Val Asp Asp Met Ala Val Arg Ile Met Ser Ala Tyr
305                 310                 315                 320
Tyr Lys Val Gly Arg Asp Arg Tyr Ser Val Pro Ile Asn Phe Asp Ser
                325                 330                 335
Trp Thr Leu Asp Thr Tyr Gly Pro Glu His Tyr Ala Val Gly Gln Gly
                340                 345                 350
Asn Thr Lys Ile Asn Glu His Val Asp Val Arg Gly Asn His Ala Glu
                355                 360                 365
Ile Ile His Glu Ile Gly Ala Ala Ser Ala Val Leu Leu Lys Asn Lys
                370                 375                 380
Gly Gly Leu Pro Leu Thr Gly Thr Glu Arg Phe Val Gly Val Phe Gly
385                 390                 395                 400
Glu Asp Ala Gly Ser Asn Pro Trp Gly Val Asn Gly Cys Ser Asp Arg
                405                 410                 415
Gly Cys Asp Asn Gly Thr Leu Ala Met Gly Trp Gly Ser Gly Thr Ala
                420                 425                 430
```

-continued

```
Asn Phe Pro Tyr Leu Val Thr Pro Glu Gln Ala Ile Glu Arg Glu Val
            435                 440                 445

Val Ser Arg Asn Gly Thr Phe Thr Ala Ile Thr Asp Asn Gly Ala Leu
450                 455                 460

Glu Gln Met Ala Ala Val Ala Ser Gln Ala Asp Val Cys Leu Val Phe
465                 470                 475                 480

Ala Asn Ala Asp Ser Gly Glu Gly Tyr Ile Asn Val Asp Gly Asn Glu
                485                 490                 495

Gly Asp Arg Lys Asn Leu Thr Leu Trp Gln Gly Ala Asp Gln Val Ile
            500                 505                 510

His Asn Val Thr Ala Asn Cys Asn Asn Thr Val Val Leu His Thr
            515                 520                 525

Val Gly Pro Val Leu Ile Asp Asp Trp Tyr Asp His Pro Asn Val Thr
530                 535                 540

Ala Ile Leu Trp Ala Gly Leu Pro Gly Gln Glu Ser Gly Asn Ser Leu
545                 550                 555                 560

Val Asp Val Leu Tyr Gly Arg Val Asn Pro Gly Gly Lys Thr Pro Phe
                565                 570                 575

Thr Trp Gly Arg Thr Arg Glu Asp Tyr Gly Ala Pro Leu Val Leu Lys
            580                 585                 590

Pro Asn Asn Gly Lys Gly Ala Pro Gln Gln Asp Phe Thr Glu Gly Ile
            595                 600                 605

Phe Ile Asp Tyr Arg Arg Phe Asp Lys Tyr Asn Ile Thr Pro Ile Tyr
            610                 615                 620

Glu Phe Gly Phe Gly Leu Ser Tyr Thr Thr Phe Glu Phe Ser Glu Leu
625                 630                 635                 640

Asn Val Gln Pro Ile Asn Thr Pro Pro Tyr Thr Pro Ala Ser Gly Phe
                645                 650                 655

Thr Lys Ala Ala Gln Ser Phe Gly Pro Ser Ser Asn Ala Ser Asp Asn
            660                 665                 670

Leu Tyr Pro Ser Asp Ile Glu Arg Val Pro Leu Tyr Ile Tyr Pro Trp
            675                 680                 685

Leu Asn Ser Thr Asp Leu Lys Ala Ser Ala Asn Asp Pro Asp Tyr Gly
690                 695                 700

Leu Pro Asn Asp Lys Tyr Val Pro Pro Asn Ala Thr Asn Gly Asn Pro
705                 710                 715                 720

Gln Pro Ile Asn Pro Ala Gly Gly Ala Pro Gly Gly Asn Pro Ser Leu
                725                 730                 735

Tyr Glu Pro Val Ala Arg Val Ser Ala Ile Ile Thr Asn Thr Gly Lys
            740                 745                 750

Val Thr Gly Asp Glu Val Pro Gln Leu Tyr Val Ser Leu Gly Gly Pro
            755                 760                 765

Asp Asp Ala Pro Lys Val Leu Arg Gly Phe Asp Arg Ile Thr Leu Ala
770                 775                 780

Pro Gly Gln Gln Thr Leu Trp Thr Thr Thr Leu Thr Arg Arg Asp Ile
785                 790                 795                 800

Ser Asn Trp Asp Pro Val Thr Gln Asn Trp Val Val Thr Asn Tyr Thr
                805                 810                 815

Lys Thr Val Tyr Val Gly Asn Ser Ser Arg Asn Leu Pro Leu Gln Ala
            820                 825                 830

Pro Leu Lys Pro Tyr Pro Gly Ile Gly His Gly His His His His His
            835                 840                 845

His
```

```
<210> SEQ ID NO 14
<211> LENGTH: 332
<212> TYPE: PRT
<213> ORGANISM: Trichoderma reesei

<400> SEQUENCE: 14

His Gly His Ile Asn Asp Ile Val Ile Asn Gly Val Trp Tyr Gln Ala
 1               5                  10                  15

Tyr Asp Pro Thr Thr Phe Pro Tyr Glu Ser Asn Pro Pro Ile Val Val
                20                  25                  30

Gly Trp Thr Ala Ala Asp Leu Asp Asn Gly Phe Val Ser Pro Asp Ala
            35                  40                  45

Tyr Gln Asn Pro Asp Ile Ile Cys His Lys Asn Ala Thr Asn Ala Lys
    50                  55                  60

Gly His Ala Ser Val Lys Ala Gly Asp Thr Ile Leu Phe Gln Trp Val
65                  70                  75                  80

Pro Val Pro Trp Pro His Pro Gly Pro Ile Val Asp Tyr Leu Ala Asn
                85                  90                  95

Cys Asn Gly Asp Cys Glu Thr Val Asp Lys Thr Thr Leu Glu Phe Phe
                100                 105                 110

Lys Ile Asp Gly Val Gly Leu Leu Ser Gly Gly Asp Pro Gly Thr Trp
            115                 120                 125

Ala Ser Asp Val Leu Ile Ser Asn Asn Asn Thr Trp Val Val Lys Ile
    130                 135                 140

Pro Asp Asn Leu Ala Pro Gly Asn Tyr Val Leu Arg His Glu Ile Ile
145                 150                 155                 160

Ala Leu His Ser Ala Gly Gln Ala Asn Gly Ala Gln Asn Tyr Pro Gln
                165                 170                 175

Cys Phe Asn Ile Ala Val Ser Gly Ser Gly Ser Leu Gln Pro Ser Gly
                180                 185                 190

Val Leu Gly Thr Asp Leu Tyr His Ala Thr Asp Pro Gly Val Leu Ile
            195                 200                 205

Asn Ile Tyr Thr Ser Pro Leu Asn Tyr Ile Ile Pro Gly Pro Thr Val
210                 215                 220

Val Ser Gly Leu Pro Thr Ser Val Ala Gln Gly Ser Ser Ala Ala Thr
225                 230                 235                 240

Ala Thr Ala Ser Ala Thr Val Pro Gly Gly Gly Ser Gly Pro Thr Ser
                245                 250                 255

Arg Thr Thr Thr Thr Ala Arg Thr Thr Gln Ala Ser Ser Arg Pro Ser
            260                 265                 270

Ser Thr Pro Pro Ala Thr Thr Ser Ala Pro Ala Gly Gly Pro Thr Gln
    275                 280                 285

Thr Leu Tyr Gly Gln Cys Gly Gly Ser Gly Tyr Ser Gly Pro Thr Arg
            290                 295                 300

Cys Ala Pro Pro Ala Thr Cys Ser Thr Leu Asn Pro Tyr Tyr Ala Gln
305                 310                 315                 320

Cys Leu Asn Ala Ser Ala His His His His His His
                325                 330
```

POLYPEPTIDES HAVING XYLANASE ACTIVITY WITH A HIGH CONVERSION RATE OF XYLOSE—CONTAINING POLYSACCHARIDES

CROSS REFERENCE TO RELATED APPLICATIONS

This application claims the priority of PCT/EP2015/069351, filed on 24 Aug. 2015, which claims priority to European Patent Application No. 14003017.2, filed on 2 Sep. 2014, the entire contents of each of which are hereby incorporated in total by reference.

SEQUENCE LISTING

This application incorporates by reference the Sequence Listing contained in an ASCII text file named "366746_90031_Sequence.txt" submitted via EFS-Web. The text file was created on Feb. 23, 2017, and is 44 kb in size.

The present application provides novel polypeptides having xylanase activity and the respective nucleic acid sequences encoding those polypeptides as well as vectors comprising these nucleic acid sequences and host cells transformed by these vectors. In addition the present invention provides a method for producing these polypeptides and a composition comprising the inventive polypeptides.

Hemicelluloses and particularly xylan-containing polysaccharides are a valuable source for the production of monosaccharides which can be converted into biofuels, industrial platform chemicals, consumer products, food and feed additives. Due to the heterogeneous chemical structure of this material its degradation requires a series of physico-chemical and/or enzymatic treatment steps. Processes enabling an effective complete or selective hydrolysis of pentose-containing polysaccharides are highly desirable.

An important source of pentoses from biomass is xylan. Xylan constitutes about 15 to 25 wt.-% of lignocellulosic biomass and up to 70 wt.-% of other feedstocks such as oat spelts. Xylans represent one of the major components of plant cell walls and constitute major parts of agricultural waste products, e.g. wheat straw, corn stover, corn cobs, and cotton seed. Xylans consist of xylose monomeric subunits linked by β-1-4-glycosidic bonds in a complex polymer with various other components such as arabinose, glucuronic acid, methylglucuronic acid, and acetyl groups. In cereals, xylans frequently contain side chains of α-1,2- and/or α-1,3-linked L-arabinofuranoside. These substituted xylans are commonly referred to as arabinoxylans. Xylans that are substituted with glucose are referred to as glucoxylans. Also mixed forms of these xylans exist.

Xylanases (β-1,3- or β-1,4-xylan xylohydrolase; E.C. 3.2.1.8) are xylanolytic enzymes that depolymerize xylan, arabinoxylan, and/or other xylose-containing polysaccharides. Endo-xylanases (e.g. endo-β-1,4-xylanase) hydrolyze the internal β-glycosidic linkages in xylan, arabinoxylan, and/or other xylose-containing polysaccharides to produce smaller molecular weight xylo-oligomers or xylose monomers.

Major industrial applications of xylanases today are for example in the pulp and paper industry to improve the bleachability of pulps and the food industry to produce xylose as basis for the sweetener xylitol. Furthermore, xylanases can be used in food and feed compositions which contain cereals (e.g. barley, wheat, maize, rye, triticale, or oats) or cereal by-products that are rich in xylans, arabinoxylans and/or glucoxylans. Addition of xylanases to animal feed or baking products improves the break-down of plant cell walls which leads to better utilization of plant nutrients and/or prolonged bread freshness, respectively. In feed compositions xylanase addition leads to improved animal growth rate and feed conversion. Additionally, the viscosity of feed compositions containing xylan can be reduced by xylanase leading to better acceptability and adsorption.

Despite the relatively high number of known fungal and bacterial xylanases, the number of xylanases which do not only serve the intended purpose but also industrially applicable (and thus commercially profitable) remains limited. This is mainly due to particular physical process conditions, such as high temperature and specific pH conditions, as well as lack of substrate and/or product selectivity and compatibility of the particular xylanase leading to low conversion rates. Such drawbacks limit the use of xylanases.

As transformation of biomass such as cellulose- and lignocellulose-containing biomass of various origins to valuable products is gaining more and more importance, there is an increasing need for xylanases which enable efficient and industrially applicable conversion. Within the EP 2 336 152 highly efficient xylanases with enhanced thermostability are disclosed. To even more increase efficiency of product generation and purification, further improvements are, however, mandatory.

The inventors of the present invention have therefore set themselves the task to develop novel xylanases which allow efficient product generation due to high conversion rates also of recalcitrant substrates such as xylose-containing polysaccharides. In addition, a high substrate compatibility and ability of synergistic interaction with other enzymes should lead to further process intensification and further cost reduction. Finally, the xylanases should also show a high temperature and pH stability.

The inventors of the present invention have now surprisingly found that this task can be solved by polypeptides having xylanase activity with a high conversion rate of xylose-containing polysaccharides, wherein the polypeptide comprises an amino acid sequence having at least 75% sequence identity to SEQ ID No: 2.

The term "xylanase activity" refers to all polypeptides which are capable of catalyzing the hydrolysis of β-1,3- or β-1,4-xylosidic linkages with the release of smaller molecular weight xylo-oligomers or xylose monomers. The term "xylanase" is defined herein as a β-1,3- or β-1,4-xylan xylohydrolase (E.C. 3.2.1.8).

The term "xylose-containing polysaccharides" refers to any substrate containing xylose oligomers such as xylotetranose, xylopentanose, xylohexanose or xylose polymers such as xylan or hemicellulose. Examples for xylose-containing polysaccharides are wheat straw, wood, cereal straw and/or husks, corn stover, bagasse, oat hulls, switch grass, cellulose, raw paper pulp (obtained from pulp and paper production) and mixtures thereof and other kind of lignocellulosic plant material.

The nomenclature of amino acids, peptides, nucleotides and nucleic acids is done according to the suggestions of IUPAC. Generally amino acids are named within this document according to the one letter code.

The term "high conversion rate of xylose-containing polysaccharides" refers to the ability to convert at least 60 wt.-% of the xylose-containing polysaccharides of a certain substrate to xylose and/or xylose-containing oligosaccharides and glucose, preferably at least 70 wt.-%, more preferred at least 75 wt.-%, even more preferred at least 80 wt.-%, particularly preferred at least 85 wt.-% and most preferred at least 90 wt.-% when subjecting neutral steam-exploded wheat straw to the polypeptide at pH 5 and 50° C. for 24 hours.

Within a further preferred embodiment, the polypeptides according to the present invention convert xylose-containing polysaccharides to xylose and/or xylose-containing oligosaccharides and glucose monomers in a weight ratio of at least 5:1, preferably 7:1 and most preferred 10:1 when subjecting neutral steam-exploded wheat straw to the polypeptide at pH 5 and 50° C. for 24 hours.

The polypeptide according to the present invention comprises an amino acid sequence having at least 75% sequence identity, preferably at least 77%, further preferred at least 80%, particularly preferred at least 85%, even more preferred at least 90%, also preferred at least 95%, furthermore preferred at least 98% and most preferred at least 99% sequence identity to SEQ ID No: 2.

The polypeptide according to the present invention preferably comprises a signal peptide which is cleaved off during secretion into the supernatant.

The polypeptide according to the present invention preferably comprises a polypeptide chain of more than 250 amino acids. More preferably, the length is between 290 and 500 amino acids, even more preferably between 320 and 400 amino acids. Most preferably the polypeptide comprises between 379 and 390 amino acid residues.

The polypeptide according to the present invention preferably has a molecular weight of more than 30 kD. More preferably, the size is between 32 and 45 kD, even more preferably between 34.5 and 42.5 kD. Most preferably the polypeptide has a size between 40 and 42 kD. A particularly suitable size is 41.9 kD of the unmodified polypeptide molecule.

Furthermore, it is particularly preferred that the amino acid sequence of the polypeptide has the sequence as defined by SEQ ID No: 2 or SEQ ID No: 4 wherein 1 to 30 amino acid residues are substituted, deleted, or inserted (all also referred to as "mutations").

Particularly preferred are variants of the protein of SEQ ID NO: 2. "Protein variants" are polypeptides whose amino acid sequence differs in one or more positions from this parental protein, whereby differences might be replacements of one amino acid by another, deletions of single or several amino acids, or insertion of additional amino acids or stretches of amino acids into the parental sequence. Per definition variants of the parental polypeptide shall be distinguished from other polypeptides by comparison of sequence identity (alignments) using the ClustalW Algorithm (Larkin M. A., Blackshields G., Brown N. P., Chenna R., McGettigan P. A., McWilliam H., Valentin F., Wallace I. M., Wilm A., Lopez R., Thompson J. D., Gibson T. J. and Higgins D. G. (2007) ClustalW and ClustalX version 2. Bioinformatics 2007 23(21): 2947-2948). Methods for the generation of such protein variants include random or site directed mutagenesis, site-saturation mutagenesis, PCR-based fragment assembly, DNA shuffling, homologous recombination in-vitro or in-vivo, and methods of gene-synthesis.

Exchanges or substitutions of single amino acids or are described by naming the single letter code of the original amino acid followed by its position number and the single letter code of the replacing amino acid, i.e. the change of glutamine at position one to a leucine at this position is described as "Q1L". For deletions of single positions from the sequence the symbol of the replacing amino acid is substituted by the three letter abbreviation "del" thus the deletion of glutamine at position 3 would be referred to as "Q3del". Inserted additional amino acids receive the number of the preceding position extended by a small letter in alphabetical order relative to their distance to their point of insertion. Thus, the insertion of two tryptophanes after position 3 is referred to as "3aW, 3bW". Introduction of untranslated codons TAA, TGA and TAG into the nucleic acid sequence is indicated as "*" in the amino acid sequence, thus the introduction of a terminating codon at position 4 of the amino acid sequence is referred to as "T4*".

Multiple mutations are separated by a plus sign or a slash or a comma. For example, two mutations in positions 20 and 21 substituting alanine and glutamic acid for glycine and serine, respectively, are indicated as "V20G+S21T" or "V20G/S21T" "V20G,S21T".

When an amino acid residue at a given position is substituted with two or more alternative amino acid residues these residues are separated by a comma or a slash. For example, substitution of alanine at position 30 with either glycine or glutamic acid is indicated as "V20G,E" or "V20G/E", or "V20G, V20E".

When a position suitable for mutation is identified herein without any specific mutation being suggested, it is to be understood that any amino acid residue may be substituted for the amino acid residue present in the position. Thus, for instance, when a mutation of a valine in position 20 is mentioned but not specified, it is to be understood that the alanine may be deleted or substituted for any other amino acid residue (i.e. any one of R, N, D, C, Q, E, G, H, I, L, K, M, F, P, S, T, W, Y and V).

The terms "similar mutation" or e.g. "similar substitution" refer to an amino acid mutation that a person skilled in the art would consider similar to a first mutation. Similar in this context means an amino acid that has similar chemical characteristics. If, for example, a mutation at a specific position leads to a substitution of a non-aliphatic amino acid residue (e.g. Ser) with an aliphatic amino acid residue (e.g. Leu), then a substitution at the same position with a different aliphatic amino acid (e.g. Ile or Val) is referred to as a similar mutation. Further amino acid characteristics include size of the residue, hydrophobicity, polarity, charge, pK-value, and other amino acid characteristics known in the art. Accordingly, a similar mutation may include substitution such as basic for basic, acidic for acidic, polar for polar etc. The sets of amino acids thus derived are likely to be conserved for structural reasons. These sets can be described in the form of a Venn diagram. Similar substitutions may be made, for example, according to the following grouping of amino acids: Hydrophobic: F W Y H K M I L V A G; Aromatic: F W Y H; Aliphatic: I L V; Polar: W Y H K R E D C S T N; Charged H K R E D; Positively charged: H K R; Negatively charged: E D.

As convention for numbering of amino acids and designation of protein variants for the description of protein variants the first glutamine (Q) of the amino acid sequence Q A Q T W G within the parental protein sequence given in SEQ ID NO: 4 is referred to as position number 1 or Q1 or glutamine 1. The numbering of all amino acids will be according to their position in the parental sequence given in SEQ ID No: 2 relative to this position number 1.

Within a particular preferred embodiment, the present invention provides the novel polypeptide FfXyn1 (SEQ ID No: 2). Furthermore, the polypeptides mFfXyn1 (SEQ ID No: 4) comprising the respective mature protein as well as fusions with N-terminal signal peptides, exemplified by the coding nucleic acids of SEQ ID No: 4 and SEQ ID No: 5, are provided within particularly preferred embodiments.

The present invention also provides fusion proteins of the polypeptide of the present invention with other protein sequences. Such sequences can represent catalytically active proteins, binding proteins, proteins influencing aspects of the cellular expression or sequences influencing chemical, catalytic, biological or physical properties of the fused target protein, or being without particular effect. The fusions also include those containing only parts of the target sequence, wherein this part contributes to the enzymatic activity of the fusion protein. Of special interest among the fusions with catalytically active proteins are those with proteins selected from the group of carbohydrate-modifying enzymes. Of special interest among the fusions with binding proteins are those made with binding modules from carbohydrate-modifying enzymes. It is well known that such fusions can beneficially influence the enzymatic and physical properties of the fused parts, especially those of the target protein.

Within a particular preferred embodiment of the present invention the polypeptide according to the present invention is fused with a carbohydrate-binding module with special affinity to xylan or other polymeric sugars found in hemicellulose.

Within an even more preferred embodiment of the present invention the fusion partners of the polypeptide according to the present invention are selected from carbohydrate-binding module (CBM) sequences from the classes 13, 15, 22, 31, 35, 36 or 37 (CAZy database; Cantarel B L, Coutinho P M, Rancurel C, Bernard T, Lombard V, Henrissat B (2009) The Carbohydrate-Active EnZymes database (CAZy): an expert resource for Glycogenomics. Nucleic Acids Res 37:D233-238 [PMID: 18838391]).

Further preferred CBM fusion partners of the polypeptide according to the present invention are selected from class 13 are the xylan-binding modules of *Streptomyces lividans* (Blast Entry no. AAC26525.1) and *Aspergillus fumigatus* Af293 (Blast Entry no. EAL91233.1).

Further preferred fusion partners of the polypeptide according to the present invention are the CBMs of *Thermobifida fusca* (Blast Entry no. AAZ55678.1) and *Teredinibacter turnerae* T7901 (Blast Entry no. ACS93528.1).

Further preferred CBM fusion partners for the polypeptide according to the present invention from class 22 are the xylan-binding modules of *Paenibacillus barcinonensis* (Blast Entry no. CAA07173.1), *Thermoanaerobacterium saccharolyticum* (Blast Entry no. AAC43719.1) or *Xylanimicrobium pachnodae* (Blast Entry no. AAD54768.1), *Cellulomonas fimi* (Blast Entry no. CAA90745.1) or *Caldicellulosiruptor* sp. Rt69B.1 (Blast Entry no. AAB95326.1).

A further preferred CBM fusion partner of the polypeptide according to the present invention selected from class 36 is the xylan-binding modules of *Clostridium phytofermentans* ISDg (Blast Entry no. ABX42059.1).

A further preferred CBM fusion partner of the polypeptide according to the present invention selected from class 37 is the xylan-binding modules of *Ruminococcus albus* 8 (Blast Entry no. AAT48119.1).

A further preferred CBM fusion partner of the polypeptide according to the present invention is the class 1 cellulose binding module of *Trichoderma reesei* cellobiohydrolase 1 (Blast Entry no. XP_006969224).

The polypeptides according to the present invention are also characterized by high thermal process stability. Preferably, the polypeptide according to the present invention maintains at least 80%, more preferably more than 85%, even more preferred at least 90%, particularly at least 95% and most preferred at least 99% of its xylanase activity after 4 hours incubation in 50 mM phosphate buffer at 50° C.

Activity at elevated temperatures of the polypeptide according to the present invention is determined by measuring xylan hydrolysis at various temperatures for a certain amount of time under the following conditions: pH 5, 2% w/w dry weight substrate concentration, enzyme:xylan ratio (E/S) of 1% wt./wt. dry weight.

The polypeptide according to the present invention preferably shows optimum xylanase activity in the temperature range of from 40 to 77° C. Most preferably, the polypeptide according to the present invention shows xylanase activity in the temperature range of from 45 to 70° C. and most preferred of from 50 to 65° C. In this context, the term "optimum xylanase activity" is to be understood as temperature which leads to the highest release of reducing sugar-ends when incubating the enzyme with xylan for 30 minutes at pH 5.

The polypeptide according to the present invention is also characterized by a wide pH activity profile. Within a preferred embodiment, the polypeptide according to the present invention is active over a pH range from 5.0 to 5.5, more preferred from 4.0 to 6.0 and most preferred from 3.5 to 8.5. The term "active at pH" is to be understood as a minimum of 10% remaining activity at the pH of the measurement compared to the maximum pH-activity when incubating the enzyme with xylan for 30 minutes at 50° C.

The polypeptide according to the present invention is also characterized by high protease stability. Within a preferred embodiment the polypeptide according to the present invention maintains at least 80%, preferably at least 85%, particularly preferred at least 90% and most preferred at least 95%, of its xylanase activity after having been subjected to trypsin at pH of 7.8 and a temperature of 50° C. for 1 hour.

Within a preferred embodiment the polypeptide according to the present invention maintains at least 80%, preferably at least 85%, particularly preferred at least 90% and most preferred at least 95%, of its xylanase activity after having been subjected to pepsin at pH of 3 and a temperature of 37° C. for 2 hours.

The polypeptide according to the present invention is also characterized by high expression and high secretion rates from various microorganisms, in particular by secretion from fungal and/or yeast hosts. More preferably, the polypeptide according to the present invention is expressed and secreted at a level of more than 100 mg/l, preferably at a level of more than 500 mg/l, particularly preferred at a level of more than 750 mg/l, even more preferred at a level of 1 g/l and most preferred at a level of 1.25 g/l into the supernatant after introduction of a promotor functionally linked to a nucleic acid encoding the polypeptide into a suitable expression host. Promotors disclosed within the present application are preferred.

A suitable expression host is preferably yeast, more preferably a yeast of the genus *Saccharomyces, Kluyveromyces, Schizosaccharomyces, Candida, Yarrowia, Komagataella, Pichia, Hansenula*; particularly selected from the group *Saccharomyces cerevisiae, Schizosaccharomyces pombe, Kluyveromyces marxianus, Yarrowina lipolytica, Hansenula polymorpha, Pichia angusta, Komagataella pastoris* and *Pichia pastoris*.

Another suitable expression host is a bacterium. Particularly suitable expression hosts are *Lactococcus lactis, Lactobacillus brevis, Bacillus subtilis, Bacillus megaterium, Bacillus lentus, Bacillus amyloliquefaciens, Bacillus licheniformis, Pseudomonas fluorescence, Klebsiella planticola* and *Escherichia coli*.

Another suitable expression host is a fungus, selected from the genus *Penicillium, Trichoderma, Hypocrea, Asper-*

*gillus, Cantharellu, Boletos, Agraicus, Pleurotus, Trametes, Phanerochaete, Myceliophthora, Chaetomium, Humicola, Chrysosporium, Talaromyces* and *Neurospora*. Particularly suitable expression hosts are *Aspergillus niger, Aspergillus oryzae, Aspergillus nidulans, Penicillium chrysogenum, Trichoderma reesei, Myceliophthora thermophila, Chrysosporium lucknowense, Trichoderma viridae, Trichoderma harzianum, Hypocaea pseudokonigii* and *Talaromyces emersonii*.

Methods of determining expressibility, i.e. yield of a secreted protein and/or enzyme in the supernatant of a culture are known to a person skilled in the art.

The present invention further provides a nucleic acid encoding the polypeptide according to the present invention having an amino acid sequence with at least 70% sequence identity to SEQ ID No: 1, No: 3, No: 5 or No: 6. In a preferred embodiment, a nucleic acid encoding a polypeptide having an amino acid sequence with at least 75% sequence identity, preferably at least 80%, further preferred at least 85%, particularly preferred at least 90%, even more preferred at least 92%, also preferred at least 95%, furthermore preferred at least 98% and most preferred at least 99% sequence identity to SEQ ID NO: 1 (encoding FfXyn1) in the original and the mature form (SEQ ID NO: 3) as well as fusions with signal peptides for the enhanced heterologous production in filamentous fungi like *Trichoderma reesei* (SEQ ID NO: 5) and yeasts such as *Saccharomyces cerevisiae* (SEQ ID NO: 6) are provided.

In a further preferred embodiment, the nucleic acid encodes a polypeptide according to the present invention having the sequence as defined by SEQ ID No: 1, No: 3, No: 5 or No: 6, wherein 1 to 30 nucleic acids are substituted, deleted or inserted (all referred to as "mutations"). Mutations within the coding region of the amino acid sequence, the protein structure and/or the active center of the xylanase are particularly preferred.

The term "mutation" comprises any kind of nucleotide sequence modification including insertions, deletions, points mutations, inversions, or combinations thereof. The definitions regarding amino acid sequence modifications and mutations apply accordingly.

The present invention further provides vectors comprising a nucleic acid of the present invention. The definitions regarding the inventive nucleic acid sequences apply accordingly.

Examples for episomally maintained vectors are derivatives of bacterial plasmids, yeast plasmids, centromer based linear DNA, constructs of viral origin like SV40, phage DNA, fungal ARS based DNA-vehicles, baculovirus, vaccinia, adenovirus, fowl pox virus, and pseudorabies as well as vectors derived from combinations of plasmids and phage or viral DNA.

A suitable expression vector according to the present invention may comprise one or more genetic elements representing promotor sequences, transcription initiation sites, elements for the initiation of translation, and functional elements for protein export that are translationally coupled to the nucleic acid according to the present invention.

The vector according to the present invention may encode more than one polypeptide including more than one xylanase or may encode a fusion polypeptide comprising the xylanase according to the invention.

The vector according to the present invention may be episomally maintained in the host cell or integrated into the chromosome of the host.

The present invention further provides a host cell transformed with a vector according to the present invention. The host cell according to the present invention may be used for recombinant protein production or for metabolic transformation of xylose containing substrates to preferred metabolites.

The recombinant host cell according to the present invention is preferably selected from bacteria, yeast, or fungal cells. In a particularly preferred embodiment, the host cell is selected from the group consisting of *Escherichia, Klebsiella, Pseudomonas, Lactobacillus, Bacillus, Streptomyces; Saccharomyces, Kluyveromyces, Schizosaccharomyces, Candida, Yarrowia, Komagataella, Pichia, Hansenula, Penicillium, Trichoderma, Hypocrea, Aspergillus, Cantharellu, Agraicus, Boletos, Pleurotus, Trametes, Phanerochaete, Myceliophthora. Chaetomium, Humicola, Chrysosporium, Talaromyces* and *Neurospora*.

Preferably, the host cell is selected from *Lactococcus lactis, Lactobacillus brevis, Bacillus subtilis, Bacillus megaterium, Bacillus lentus, Bacillus amyloliquefaciens, Bacillus licheniformis, Pseudomonas fluorescence, Klebsiella planticola, Escherichia coli, Streptomyces lividans, Saccharomyces cerevisiae, Schizosaccharomyces pombe, Kluyveromyces marxianus, Yarrowina lipolytica, Hansenula polymorpha, Pichia angusta, Komagataella pastoris, Pichia pastoris, Aspergillus niger, Aspergillus oryzae, Trichoderma reesei* and *Myceliophthora thermophile*.

The recombinant host cell according to the present invention may comprise one or more vectors according to the present invention.

A further aspect of the invention includes expression cassettes allowing the expression of the polypeptide according to the present invention, particularly of the FfXyn1 protein, in vivo or in vitro.

An expression cassette preferably comprises a promotor region upstream to the coding sequence of the gene encoding the polypeptide according to the present invention, preferably the FfXyn1 gene, sites involved in the formation of the translation initiation complex, optional regulatory sequence elements such as repressor binding or enhancer sites and optional a transcription termination sequence. Promotors may contain sequences allowing the binding of protein factors required for the transcription of coding sequence or functional mRNA. Furthermore sequences of the promotor may influence the effectiveness of transcription under a given physiological or chemical condition. A promotor may comprise elements in close proximity to the coding region or situated in more distant regions acting as enhancers. Promotors may be of prokaryotic, eukaryotic, archeal or viral origin or synthetic in nature. Preferred promotors include bacterial promotors of beta galactosidase (lacZ) gene, the tryptophane operon promotor (trp), tetracycline resistance gene promotor (tet), the araBAD promotor, virus-derived promotors T7, T3, PL or PR. Preferred promotors for the expression in yeast include glyceraldehyde phosphate dehydrogenase (GAP) promotor, hexokinase promotor, alcohol dehydrogenase ADE2 promotor, GAL1, GAL10, TEF and promotors of the methanol metabolic pathway of methylotrophic yeasts such as AOXI, MOXI or FMDH, as well as the copper-inducible CUP1 promotor. Preferred promotors for the expression in filamentous fungi include those from the celluloytic enzymes, such as CBHI, CBHII, or EGI or II, □-amylase, glucoamylase, phosphoglycerate kinase (pgk), and any promotor of genes of the glycolytic pathway.

Expression levels of a gene encoding the polypeptide according to the present invention can be increased by adjustment of the copy-number of the gene introduced into the host cells, preferably resulting in more than single copies of the gene. For optimized expression of the gene, the promotor can be regulated, either by induction following the addition of a chemical inducer by adjustment of a physical parameter. Examples for inducible systems include tetracycline repressor system, Lac repressor system or the temperature inducible □□PL promotor. Alternatively, de-repression of the promotor by reaching a suitable physiological state in the culture can be a useful strategy (Promotor of PhoA, Trp, Adh2, Fmdh, CBHI). Application of strong stationary promotors might be preferable in other situations (GAP, TEF).

A translational coupling of signal peptide sequences canced be used for the directing of the expressed polypeptide according to the present invention to cellular compartments, organelles or the export from the host cell. Signal sequences are well known in the art. Examples are leader sequences for the periplasmatic targeting from OmpA, OmpT, PelB, PhoA, glucanase or □-lactamase. Signal peptides for secretion of the proteins can be found among naturally secreted carbohydrate modifying enzymes, namely leaders from coding sequences of celloiohydrolaseI or II, endoglucanases, amyE or signal peptides of the S. cerevisiae Mfa or chicken egg lysozyme.

The expression cassette may be placed in a vector or a vector construct according to the present invention which can be episomally maintained in the host cell or integrated into the chromosome of the host. Examples for known vectors are derivatives of bacterial plasmids, yeast plasmids, centromer based linear DNA, constructs of viral origin like SV40, phage DNA, baculovirus, vaccinia, adenovirus, fowl pox virus, and pseudorabies as well as vectors derived from combinations of plasmids and phage or viral DNA. Integration of the expression cassette can be achieved by homologous recombination, transposition or by application of viral integration systems. Additionally the use of episomally maintained constructs as basis for the integration of the expression cassette copies into the chromosomal DNA is possible. Finally, any system leading to the replication of the expression cassette in the host cells is suitable as a vector or vector-construct.

In an embodiment of the invention the transferred DNA comprises further open reading frames coding for enzymes, wherein such further reading frames can be physically connected in continuous DNA strands or as a mixture of individual DNA strands. In a preferred embodiment these additional open reading frames are functionally connected to promotor elements or regulatory DNA elements themselves, thus leading to individually or co-regulated expression of the additional open reading frames in the transformed host cell. In a preferred embodiment, the additional open reading frames comprise at least one sequence selected from those coding for endo-xylanases, xyloglucanases, xylosidases, acetylxylan esterases, feruolic acid esterases, end-cellulases, exo-cellulases, arabinofuranosidases, galactanases, phytases, polysaccharide monooxygenases or arabinases.

Preferred methods for the introduction of the expression cassette constructs into the host cell include transformation, transfection, conjugation and/or interbreeding. The transformation can be achieved by DNA transfer via electroporation, protoplast fusion, lipofection, ballistic bombardment, chemical transformation based on lithium acetate, calcium chloride, PEG or manganese chloride. Further strategies include the application of viral particles. A further alternative is the application of naturally competent organisms as host cells.

Methods for further increasing the yield of the expressed protein include the co-expression of helper proteins involved in translation, trafficking of proteins, folding of proteins (e.g. Chaperones hsp70-family proteins, protein disulfide isomerase) or correct processing of the polypeptide (Kex-protease, Ste-proteases) and other events contributing to the cellular production of the protein.

After transformation of the host strain with a vector of the present invention and growth to an appropriate cell density, the selected inducible promotor is induced by temperature shift or chemical induction and cells cultured to yield the recombinant enzyme. Preferably, the polypeptide according to the present invention is produced with a signal peptide that directs the recombinant protein to be secreted from the host cell. Cells are then removed by centrifugation or filtration and the polypeptide-containing supernatant is retained.

The invention also provides methods of preparing the polypeptide according to the present invention, comprising the steps:

a) obtaining a host cell, which has been transformed with a vector comprising the nucleic acid as defined within the present invention;

b) cultivation of the host cell under conditions under which the polypeptide is expressed; and c) recovery of the polypeptide.

All definitions within the present application, particularly the definitions regarding the polypeptide, host cell, vector and nucleic acid, apply accordingly.

Cultivation of the host cell of the present invention is carried out according to methods and conditions well known to a person skilled in the art. Preferably the host cells can be cultivated on cultivation substrate from agricultural waste and/or residue streams. Agricultural waste and residues are obtained and recovered from farming and forestry and comprise parts of the harvest that cannot be converted to the main product for physical, chemical, economical or political reasons. Examples for such cultivation substrate are wheat straw, bagasse, sugar cane leaves, sugar beet pulp, low quality paper pulp, waste paper, saw dust or other residues from lumber mills. In a particular preferred embodiment the cultivation substrate has been subjected to the inventive protein prior to the cultivation or alternatively is split into two streams, whereas the other stream not used for cultivation is treated with at least the inventive protein. In a particularly preferred embodiment the inductor of the transformed host cell is released from the cultivation substrate during the treatment of the cultivation substrate with at least the inventive protein. Examples of such inducers are xylose, glucose, arabinose, rhamnose and oligomers comprising such sugar moieties.

Recovery of the polypeptide according to the present invention is carried out according to methods and conditions well known to a person skilled in the art. Within a preferred embodiment the enzyme is recovered and purified from the supernatant by methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Protein refolding steps maybe used within particularly preferred embodiments.

Within a preferred embodiment, the host cell is a yeast cell and the xylanase protein has a sequence as defined by SEQ ID No: 2 or No: 4, wherein—a particularly preferred embodiment—1 to 30 amino acid residues are substituted, deleted, or inserted, is expressed. In a particular preferred embodiment the xylanase is equipped with an affinity tag, for example a 6x-His TAG.

The present invention further provides a composition comprising the polypeptide according to the present invention. The composition preferably contains from 0.01 to 50 wt.-% (refers to the total protein content of the composition) of the polypeptide according to the present invention, further preferred from 1 to 35 wt.-% of the polypeptide according to the present invention, particularly preferred from 5 to 20 wt.-% and most preferred from 8 to 12.5 wt.-%.

Within a preferred embodiment, the composition also comprises at least one cellulase. The at least one cellulase is preferably selected from cellulase mixtures obtained from respective cellulase secreting microbial cultures. In a preferred embodiment microbial cultures for this purpose are selected from cultures of Trichoderma reesei, Myceliophthora thermophila, Talaromyces emersonii, Trichoderma viride, Penicillium verruculosum, Talaromyces stripitatus, Humicula grisaea, Chaethomium thermophilum, Humicola inculens, Clostridium thermocellum, Thermobifida fusca, Caldicellulosiruptor owenensis, Aspergillus fumigatus, Aspergillus niger, Neurospora crassa and mixtures thereof.

Within a further preferred embodiment the composition comprises one or more enzyme activities selected from cellulases, GH61 pyranose monooxygenases (also referred to as "GH61 protein"), endo-xylanases, xyloglucanases, xylosidases, acetylxylan esterases, feruolic acid esterases, beta-glucosidases, arabinofuranosidases, galactanases and arabinases.

Within a particularly preferred embodiment, the composition of the present invention is embedded in a cellulase mixture, which is enhanced by this particular addition with respect to the hydrolysis performance on cellulose, xylan and other hemicellulose material. Within a most preferred embodiment, the cellulose mixture further comprises increased levels of one or more activities selected from the group of GH61 protein, xylosidase and beta-glucosidase by 5% or more with respect to the specific activity level in the cellulase mixture.

Particularly preferred compositions comprise the polypeptide according to the present invention as defined before, at least one cellulase as defined before as well as at least one endoglucanase IV wherein it is particularly preferred that the fraction of the polypeptide according to the present invention and the endoglucanase IV are from 5% (wt./wt. determined after Bradford versus BSA) polypeptide to 40% endoglucanase IV, preferably from 8% polypeptide to 25% endoglucanase IV, whereas the percentage relates to the overall amount of protein of the composition which consists preferably of cellulase. It is also preferred that the polypeptide and the endoglucanase IV are contained in the same amount.

Within a further particularly preferred embodiment, the composition of the present invention comprises the polypeptide according to the present invention as defined before, at least one cellulase as well as at least one xylosidase and/or at least one GH61 protein. Within a preferred embodiment of the present invention, the composition comprises from 30 to 99% (wt./wt. determined after Bradford versus BSA), preferably from 40 to 90%, more preferred from 50 to 80% cellulase; from 1 to 70% (wt./wt. determined after Bradford versus BSA), preferably from 5 to 50%, even more preferred from 10 to 30% and most preferred from 15 to 20% of the polypeptide according to the present invention; and xylosidase and/or GH61 protein from 1 to 25% (wt./wt. determined after Bradford versus BSA), preferably from 5 to 20% and most preferred from 10 to 15%.

The invention also provides the use of the polypeptide according to the present invention and of the composition according to the present invention for the enzymatic degradation of lignocellulosic biomass.

The invention also relates the use of the polypeptide according to the present invention in processes for the production of biofuels, pulp, paper and cellulose fibers, platform chemicals and food and feed products from complex substrates such as "xylose-containing polysaccharides".

EXAMPLES AND FIGURES

In the following the present invention is described by the examples and figures. The examples and figures are considered for illustrative purpose only and do not limit the scope of the present invention and claims in any respect.

Example 1

Temperature Optimum and pH-range

Characterization of affinity of purified tFfXyn1 polypeptide SEQ ID NO: 7 was done with respect to the pH for optimal activity between pH 4 to 7 and the residual activity after incubation at temperatures between 40 to 65° C. pre-incubation time. The activity level was determined with the substrate p-nitrophenyl-β-D-xylopyranoside (pNP-X) at 2 mg/ml substrate concentration. 50° C. and 1 hour incubation time was applied. Residual activity determination after the temperature pre-incubation step was done at pH 5. For the determination of optimal pH, the buffers as shown within table 1 were used. Release of p-nitro phenol was determined by absorbance measurement at 405 nm. Protein quantification was done using Bradford versus BSA standards. 2 mg/ml solutions of the purified tFfXyn1 were diluted in the respective application buffers.

TABLE 1

| Buffer compositions for pH-Optimum determination | | |
|---|---|---|
| pH | mM | |
| 4 | 100 | Lactic acid |
| 4.5 | 100 | Acetate |
| 5 | 100 | Acetate |
| 5.5 | 100 | Acetate |
| 6 | 100 | MES buffer |
| 6.5 | 100 | Phosphate |
| 7 | 100 | Phosphate |

The purified tFfXyn1 polypeptide shows excellent activity from pH 4 to 6 with a maximum at pH 5 and from 50 to 65° C. with a maximum around 58° C. The results are shown in FIGS. 1A&B.

Example 2

Comparison Performance of Different Xylanase Polypeptides on Neutral Straw

Hydrolysis reactions with steam exploded wheat straw (neutral conditions) were set up using 100% and 80%

(wt./wt. determined after Bradford versus BSA) fractions of SCFMX0375 (*Trichoderma reesei* with increased beta-glucosidase levels) cellulase enzyme loads for reference under conditions of 50° C. and pH5 for 24 hours.

The substitution of 20% (wt./wt. determined after Bradford versus BSA) cellulase enzyme by the tFfXyn1 (SEQ ID NO: 7) polypeptide leads to an increase in glucose and xylose yields, whereas the substitution by the same amount of different xylanases from *Thermomyces lanuginosus* (TlXyn1_GH11; SEQ ID NO: 8) and *Trichoderma reesei* (TrXyn2_GH11 SEQ ID NO: 10, TrXyn1_GH11 SEQ ID NO: 9, TrXyn4_GH30 SEQ ID NO: 11) did not lead to such drastic improvement of the hydrolysis reaction.

The 80% reaction setup was duplicated and supplemented with 20% (wt.-%/wt.-% determined after Bradford versus BSA) of the tFfXyn1 polypeptide. Degree of saccharification was determined after 24 h of saccharification under conditions of 50° C. and pH5 followed by sugar quantification on HPLC. As can be seen, the dosage of tFfXyn1 leads to the highest total sugar release. Results are shown in FIG. 2.

Example 3

Performance of tFfXyn1 on Neutral Straw in the Presence of GH61 Protein

The synergy of tFfXyn1 (SEQ ID NO: 7) with TrE-GIV_GH61 (*T. reesei* EGIV SEQ ID NO: 14) was tested by addition of various ratios (enzyme weight determined after Bradford versus BSA per dry matter substrate) of the purified tfFxyn1 and TrEGIV_GH61 as a 25% (wt./wt. determined after Bradford versus BSA) aliquote to SCFMX0375. A local maximum of 8% (wt./wt. determined after Bradford versus BSA) tFfXyn1 was demonstrated to release a maximum glucose amount from pre-treated (neutral steam-exploded) wheat-straw, when 0.5% enzyme to substrate ratios (enzyme weight determined after Bradford versus BSA per dry matter substrate) were applied and saccharification is carried out at 50° C. and pH5 for 24 hours on neutral steam exploded wheat straw. Results are shown in FIG. 3.

Example 4

Performance of tFfXyn1 on Neutral Straw in the Presence of Beta Glucosidase (TeBgl_GH3 SEQ ID NO: 13) and Endoglucanase (TrEGIV_GH61 SEQ ID NO: 14)

Effects of increased levels of beta glucosidase TeBgl_GH3 SEQ ID NO: 13 activity in the presence of tFfXyn1 and SCFMX375 with respect to glucose and xylose yields from neutral steam exploded wheat straw were evaluated. Increased levels of beta-glucosidases were found to further improve the enzymatic release of glucose from the samples in the presence of tFfXyn1 and TrEGIV_GH61. Saccharification was carried out at 50° C. and pH5 for 24 hours. The results are shown in FIG. 4.

Example 5

Co-Action of tFfXyn1 with Xylosidase

Effects of increased levels of xylosidase from *Trichoderma reseei* (TrXyl_GH3 SEQ ID NO: 12) activity in the presence of tFfXyn1 and SCFMX375 with respect to glucose and xylose yields from neutral steam exploded wheat straw were evaluated. Saccharification was carried out at 50° C. and pH5 for 24 hours. The results are shown in FIG. 5.

BRIEF DESCRIPTION OF THE FIGURES

FIG. 1A shows the pH-stability of purified tFfXyn1

SEQUENCE LISTING DESCRIPTION

Figure 1B:
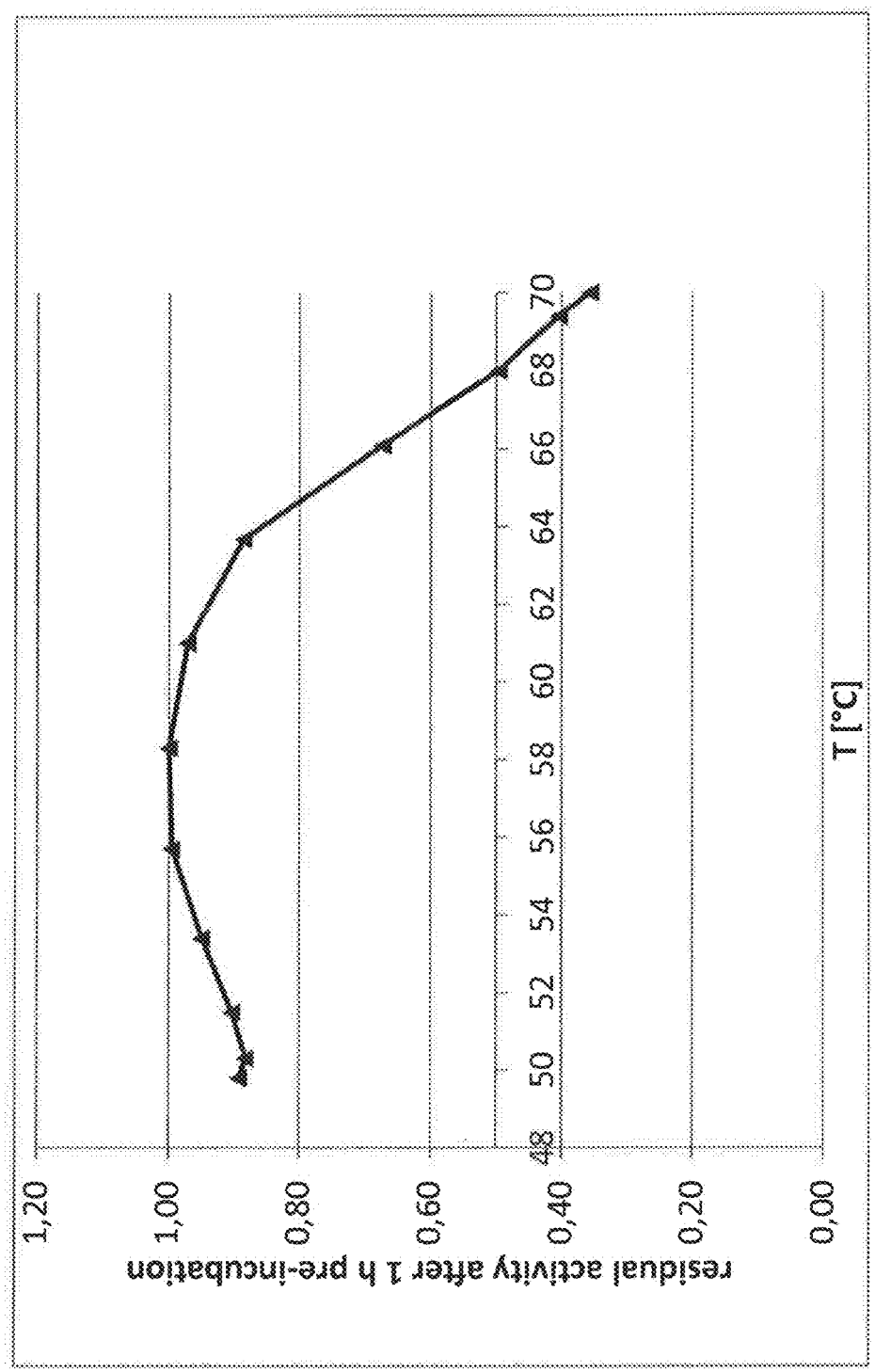
FIG. 1B shows the temperature-stability of purified tFfXyn1
Figure 2:
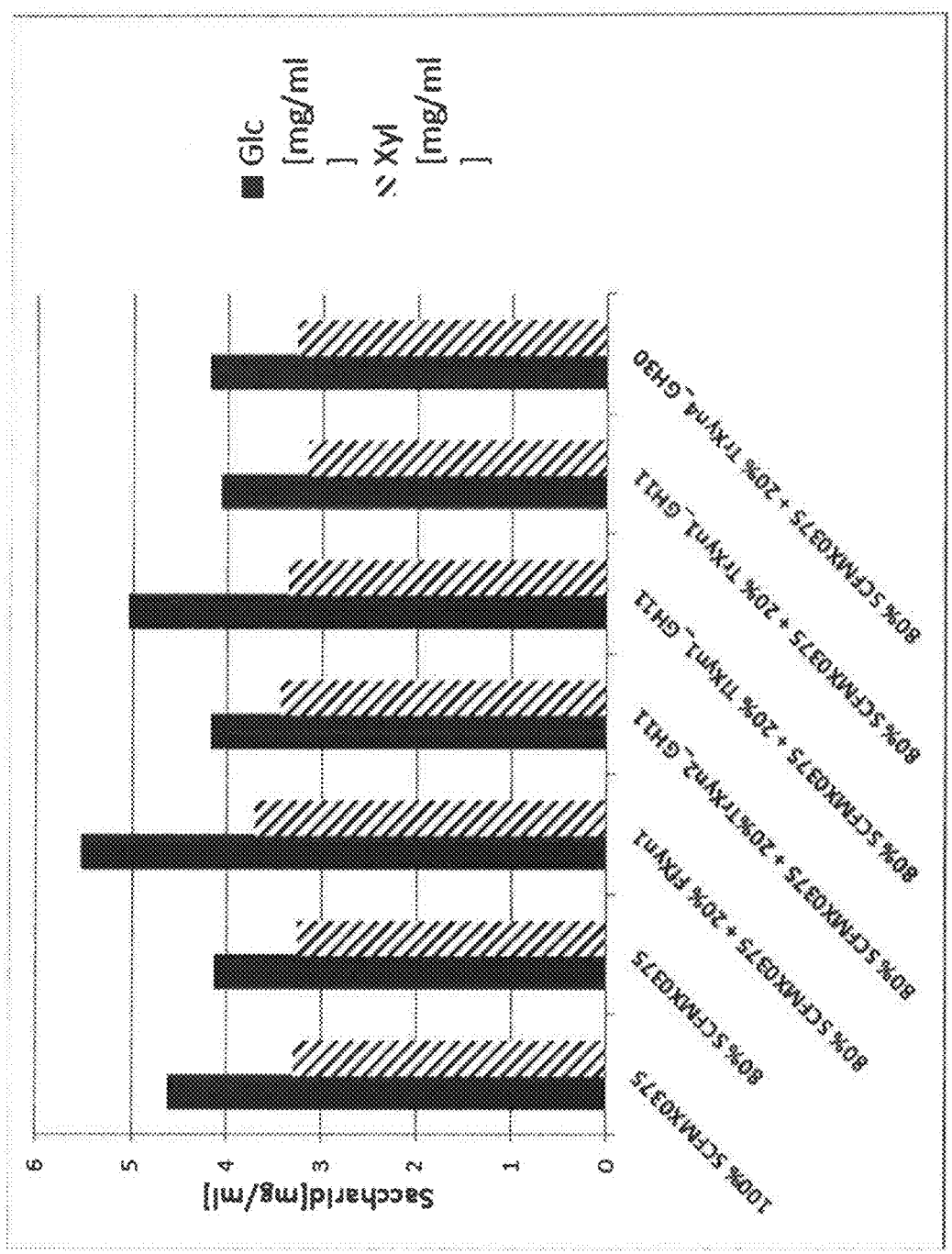
FIG. 2 shows enhanced glucose and xylose yields from saccharification reactions of neutral steam exploded wheat straw by a combination of SCFMX0375 Cellulose and tFfXyn1 in comparison to other xylanases
Figure 3:
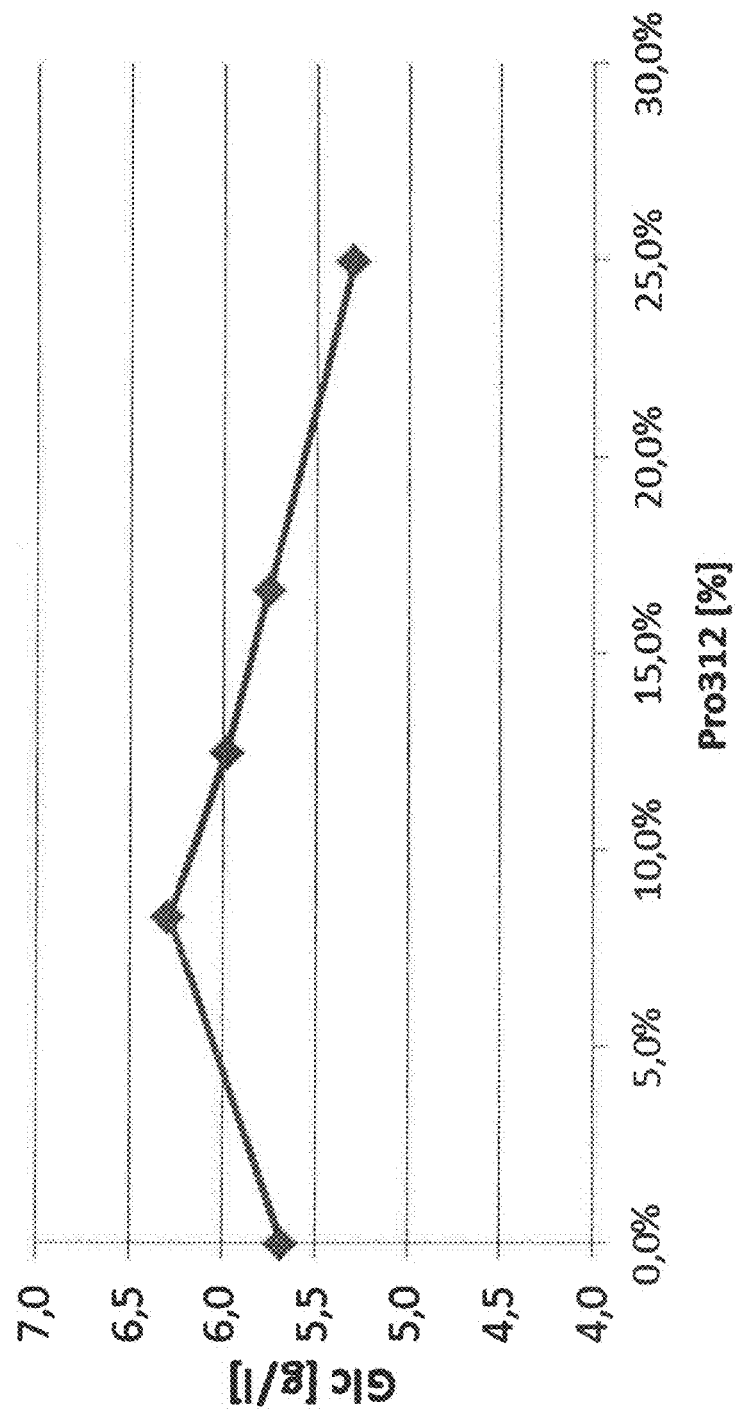
FIG. 3 shows the synergy in glucose liberation from lignocellulosic substrate between tFfXyn1 and GH61 protein
Figure 4:
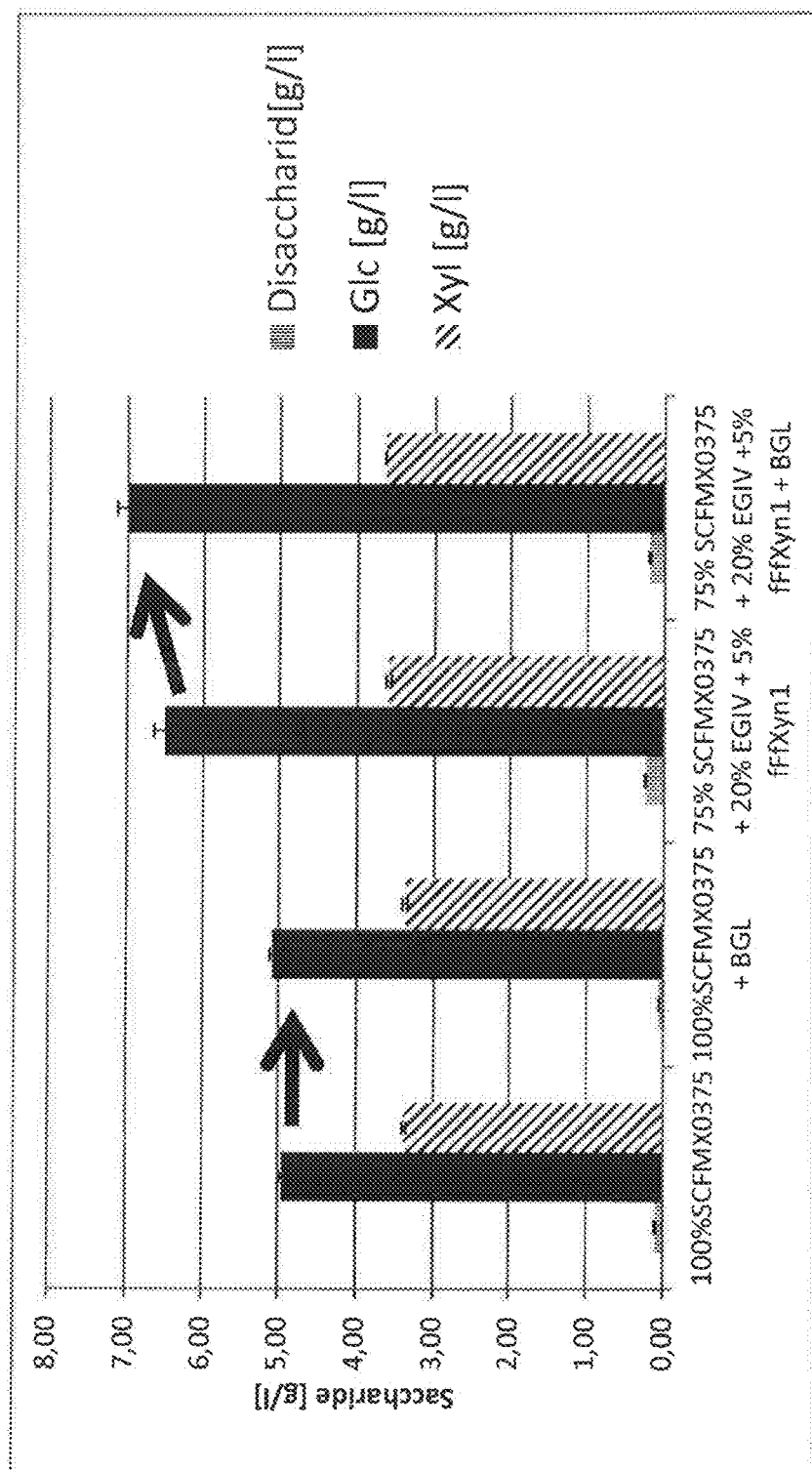
FIG. 4 shows the synergy of TeBgl_GH3 beta-glucosidase with tFfXyn1 for the monomeric sugar release from lignocellulosic substrate
Figure 5:
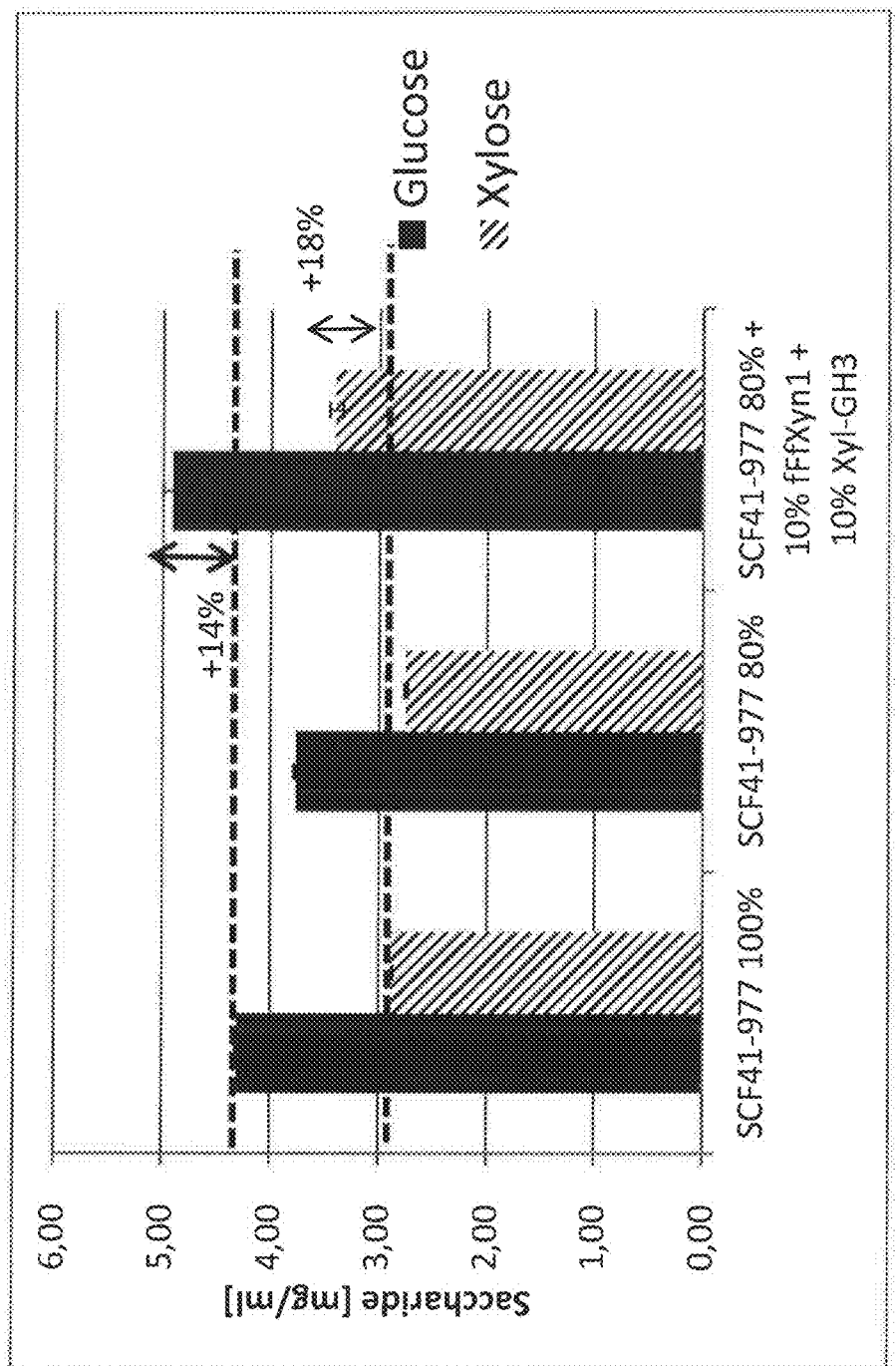
FIG. 5 shows that dosing of xylosidase significantly increases the xylose yield in the presence of tFfXyn1

SEQ ID NO: 1 DNA sequence FfXyn1 xylanase

SEQ ID NO: 2 protein sequence FfXyn1 xylanase with signal peptide

SEQ ID NO: 3 DNA sequence mFfXyn1 xylanase

SEQ ID NO: 4 protein sequence mFfXyn1 xylanase mature protein

SEQ ID NO: 5 artificial DNA sequence coding tFfXyn1 xylanase mature protein fusion with the *Trichoderma reesei* CBHI signal peptide and C-terminal 6x-His-TAG SEQ ID NO: 6 artificial DNA sequence coding yFfXyn1 xylanase mature protein fusion with the *Saccharomyces cerevisiae* MFalpha signal peptide and C-terminal 6x-His-TAG)

SEQ ID NO: 7 protein sequence tFfXyn1 xylanase mature protein fusion with the *Trichoderma reesei* CBHI signal peptide and C-terminal 6x-HIS-TAG SEQ ID NO: 8 protein sequence TlXyn1_GH11 *Thermomyces lanuginosus* xylanase mature protein SEQ ID NO: 9 protein sequence TrXyn1_GH11 *Trichoderma reesei* xylanase 1 mature protein with 6xHis-TAG)

SEQ ID NO: 10 protein sequence TrXyn2 GH11 *Trichoderma reesei* xylanase 2 mature protein with 6xHis-TAG)

SEQ ID NO: 11 protein sequence TrXyn4 GH30 *Trichoderma reesei* xylanase 4 mature protein with 6xHis-TAG SEQ ID NO: 12 protein sequence TrXyl_GH3 *Trichoderma reesei* xylosidase mature protein with 6xHis-TAG SEQ ID NO: 13 protein sequence TeBgl_GH3 *Talaromyces emersonii* beta glucosidase mature protein with 6xHis-TAG SEQ ID NO: 14 protein sequence TrEGIV_GH61 *Trichoderma reesei* endoglucanase 4 mature protein with 6xHis-TAG

What is claimed is:

1. A polypeptide having xylanase activity, wherein the polypeptide comprises a variant of SEQ ID No: 2 comprising an amino acid sequence having at least 95%, but less than 100%, sequence identity to SEQ ID No: 2 and wherein the polypeptide converts at least 60 wt.-% of the xylose-containing polysaccharides of neutral steam-exploded wheat straw to xylose and/or xylose-containing oligosaccharides, and glucose under conditions of pH 5 and 50° C. for 24 hours.

2. A polypeptide having xylanase activity, wherein the polypeptide is a variant of SEQ ID No: 2 wherein 1 to 30 amino acid residues are substituted, deleted or inserted.

3. The polypeptide of claim 1, wherein the conversion rate of lignocellulosic biomass to xylose and/or xylose-containing oligosaccharides, and glucose in a weight ratio of at least 5:1 when subjecting neutral steam-exploded wheat straw to the polypeptide at pH 5 and 50° C. for 24 hours.

4. The polypeptide of claim 1, wherein the residual xylanase activity at pH 8 and 50° C. is higher than 10% of the maximum activity at pH 8 and 50° C.

5. A composition comprising the polypeptide of claim 1.

6. The composition of claim 5, further comprising one or more activities selected from cellulases.

7. The polypeptide of claim 1, wherein said polypeptide is used for the enzymatic degradation of lignocellulosic biomass.

8. The composition of claim 5, wherein said composition is used for the enzymatic degradation of lignocellulosic biomass.

9. The polypeptide of claim 1, wherein said amino acid sequence has at least 98%, but less than 100%, sequence identity to SEQ ID No: 2.

10. The polypeptide of claim 9, wherein said amino acid sequence has at least 99%, but less than 100%, sequence identity to SEQ ID No: 2.

* * * * *